United States Patent
Lundell et al.

(10) Patent No.: US 7,326,564 B2
(45) Date of Patent: Feb. 5, 2008

(54) FLOW SYSTEM FOR MEDICAL DEVICE EVALUATION AND PRODUCTION

(75) Inventors: Beverley I. Lundell, Woodbury, MN (US); Robert L. Meisch, Crystal, MN (US); John R. Wilson, New Brighton, MN (US); Matthew W. Weston, Little Canada, MN (US); M. William Mirsch, II, Roseville, MN (US); Doug A. Page, deceased, late of Eden Prairie, MN (US); by Kathy J. Grossinger, legal representative, Eden Prairie, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 103 days.

(21) Appl. No.: 09/789,130

(22) Filed: Feb. 20, 2001

(65) Prior Publication Data

US 2002/0116054 A1 Aug. 22, 2002

(51) Int. Cl.
*C12M 3/00* (2006.01)
(52) U.S. Cl. .............................. 435/293.1; 435/284.1; 435/299.1; 623/912; 623/915
(58) Field of Classification Search ......... 435/284.1, 435/286.5, 289.1, 293.1, 298.2; 623/2.13, 623/915–918, 920–922; 137/563; 472/132; 73/37, 865.6; 366/211, 212, 218; 118/421; 134/184, 188, 189; 8/94.11
See application file for complete search history.

(56) References Cited

U.S. PATENT DOCUMENTS 2,123,463 A 7/1938 Effront ............ 435/284.1
2,673,722 A * 3/1954 Griffin et al. ............... 366/212
3,219,319 A 11/1965 Ash
3,490,438 A 1/1970 Lavender et al.
3,545,221 A 12/1970 Swenson et al.
3,639,084 A 2/1972 Goldhaber
3,734,851 A 5/1973 Matsumura
3,753,865 A 8/1973 Belzer et al.

(Continued)

FOREIGN PATENT DOCUMENTS

JP 04218147 A * 8/1992

(Continued)

OTHER PUBLICATIONS

English Language machine translation of JP-06-022745 (Feb. 1, 1994).*

*Primary Examiner*—William H. Beisner
(74) *Attorney, Agent, or Firm*—Westman, Champlin & Kelly, P.A.; Hallie A. Finucane

(57) ABSTRACT

In some embodiments, a flow system includes a medical device mount, fluid and a conduit containing the fluid and medical device mount. The conduit is mounted on an assembly that moves the conduit along with the medical device mount to induce relative motion of the fluid relative to the medical device mount. In preferred embodiments, pulsatile fluid motion is generated. In some embodiments, the fluid includes viable cells. In alternative embodiments, a flow system includes a continuous flow pump connected to a conduit loop having multiple branch conduits downstream from the pump providing alternative paths over a section of the conduit loop. Each branch conduit has a valve controlling flow through the branch. In some embodiments, at least one branch includes a medical device mount.

44 Claims, 10 Drawing Sheets

U.S. PATENT DOCUMENTS

| | | | |
|---|---|---|---|
| 3,772,153 A | 11/1973 | De Roissart | |
| 3,777,507 A | 12/1973 | Burton et al. | |
| 3,843,455 A | 10/1974 | Bier | |
| 3,893,887 A * | 7/1975 | Smith et al. | 435/395 |
| 3,956,851 A * | 5/1976 | Tapinekis | 446/267 |
| 4,025,394 A | 5/1977 | Young | |
| 4,248,972 A | 2/1981 | Fischer et al. | |
| 4,350,588 A | 9/1982 | Tsubota | |
| 4,361,484 A | 11/1982 | Larsson et al. | |
| 4,381,663 A * | 5/1983 | Swanson | 73/37 |
| 4,450,710 A | 5/1984 | Nettekoven | |
| 4,537,860 A | 8/1985 | Tolbert et al. | |
| 4,546,642 A | 10/1985 | Swanson | |
| 4,654,308 A | 3/1987 | Safi et al. | |
| 4,682,491 A | 7/1987 | Pickard | |
| 4,745,759 A | 5/1988 | Bauer et al. | |
| 4,839,280 A | 6/1989 | Banes | |
| 4,894,342 A | 1/1990 | Guinn et al. | |
| 4,931,401 A | 6/1990 | Safi | |
| 4,939,087 A | 7/1990 | Van Wie et al. | |
| 4,948,728 A | 8/1990 | Stephanopoulos et al. | |
| 5,002,890 A | 3/1991 | Morrison | |
| 5,017,490 A | 5/1991 | Taiariol et al. | |
| 5,030,575 A | 7/1991 | Stofac | |
| 5,031,527 A * | 7/1991 | Eppinger | 101/115 |
| 5,057,428 A | 10/1991 | Mizutani et al. | |
| 5,081,035 A | 1/1992 | Halberstadt et al. | |
| 5,141,861 A | 8/1992 | Dale | |
| 5,153,136 A | 10/1992 | Vandenburgh | |
| 5,171,261 A * | 12/1992 | Noishiki et al. | 623/1.41 |
| 5,176,153 A | 1/1993 | Eberhardt | |
| 5,217,899 A | 6/1993 | Shapiro et al. | |
| 5,230,693 A | 7/1993 | Williams et al. | |
| 5,266,480 A | 11/1993 | Naughton et al. | |
| 5,271,898 A * | 12/1993 | Wolf et al. | 422/64 |
| 5,272,909 A | 12/1993 | Nguyen et al. | |
| 5,279,612 A * | 1/1994 | Eberhardt | 8/94.11 |
| 5,285,657 A | 2/1994 | Bacchi et al. | |
| 5,326,706 A | 7/1994 | Yland et al. | |
| 5,338,662 A | 8/1994 | Sadri | |
| 5,362,622 A | 11/1994 | O'Dell et al. | |
| 5,368,608 A | 11/1994 | Levy et al. | |
| 5,406,853 A | 4/1995 | Lintilhac et al. | |
| 5,459,069 A | 10/1995 | Palsson et al. | |
| 5,468,605 A | 11/1995 | Harris et al. | |
| 5,476,783 A | 12/1995 | Mutsakis et al. | |
| 5,492,826 A * | 2/1996 | Townsend et al. | 435/394 |
| 5,494,822 A | 2/1996 | Sadri | |
| 5,501,971 A | 3/1996 | Freedman et al. | |
| 5,510,254 A | 4/1996 | Naughton et al. | |
| 5,512,474 A | 4/1996 | Clapper et al. | |
| 5,587,298 A | 12/1996 | Horigane et al. | |
| 5,595,910 A | 1/1997 | Kant et al. | |
| 5,597,731 A | 1/1997 | Young et al. | |
| 5,605,835 A | 2/1997 | Hu et al. | |
| 5,608,860 A | 3/1997 | Fitzpatrick et al. | |
| 5,609,835 A | 3/1997 | Pitcher | |
| 5,639,423 A | 6/1997 | Northrup et al. | |
| 5,652,143 A | 7/1997 | Gombrich et al. | |
| 5,688,687 A | 11/1997 | Palsson et al. | |
| 5,705,390 A | 1/1998 | Kadouri et al. | |
| 5,763,261 A | 6/1998 | Gruenberg | |
| 5,763,266 A | 6/1998 | Palsson et al. | |
| 5,779,996 A | 7/1998 | Stormo | |
| 5,785,926 A | 7/1998 | Seubert et al. | |
| 5,792,603 A | 8/1998 | Dunkelman et al. | |
| 5,795,710 A * | 8/1998 | Park | 435/1.1 |
| 5,821,116 A | 10/1998 | Herman | |
| 5,824,060 A * | 10/1998 | Christie et al. | 128/898 |
| 5,827,729 A | 10/1998 | Naughton et al. | |
| 5,837,522 A | 11/1998 | Swain | |
| 5,843,766 A | 12/1998 | Applegate et al. | |
| 5,846,817 A | 12/1998 | Mausli | |
| 5,846,828 A | 12/1998 | Peterson et al. | |
| 5,849,208 A | 12/1998 | Hayes et al. | |
| 5,855,610 A | 1/1999 | Vacanti et al. | |
| 5,855,620 A | 1/1999 | Bishopric et al. | |
| 5,858,721 A | 1/1999 | Naughton et al. | |
| 5,861,124 A | 1/1999 | Hosoi et al. | |
| 5,885,826 A | 3/1999 | Worden et al. | |
| 5,888,807 A | 3/1999 | Palsson et al. | |
| 5,897,997 A | 4/1999 | Louvel | |
| 5,899,937 A | 5/1999 | Goldstein et al. | |
| 5,916,800 A * | 6/1999 | Elizondo et al. | 435/284.1 |
| 5,928,945 A | 7/1999 | Seliktar et al. | |
| 5,955,029 A | 9/1999 | Wilding et al. | |
| 5,972,661 A | 10/1999 | Kubera et al. | |
| 5,985,653 A | 11/1999 | Armstrong et al. | |
| 5,993,884 A | 11/1999 | Woolf et al. | |
| 5,997,575 A | 12/1999 | Whitson et al. | |
| 6,001,585 A | 12/1999 | Gramer | |
| 6,008,049 A | 12/1999 | Naughton et al. | |
| 6,043,079 A | 3/2000 | Leighton | |
| 6,058,958 A | 5/2000 | Benkowski et al. | |
| 6,060,306 A | 5/2000 | Flatt et al. | |
| 6,077,660 A | 6/2000 | Wong et al. | |
| 6,121,042 A | 9/2000 | Peterson et al. | |
| 6,140,039 A | 10/2000 | Naughton et al. | |
| 6,174,719 B1 | 1/2001 | Elizondo et al. | |
| 6,605,463 B1 * | 8/2003 | Bader | 435/298.2 |

FOREIGN PATENT DOCUMENTS

JP     06022745 A  *  2/1994

\* cited by examiner

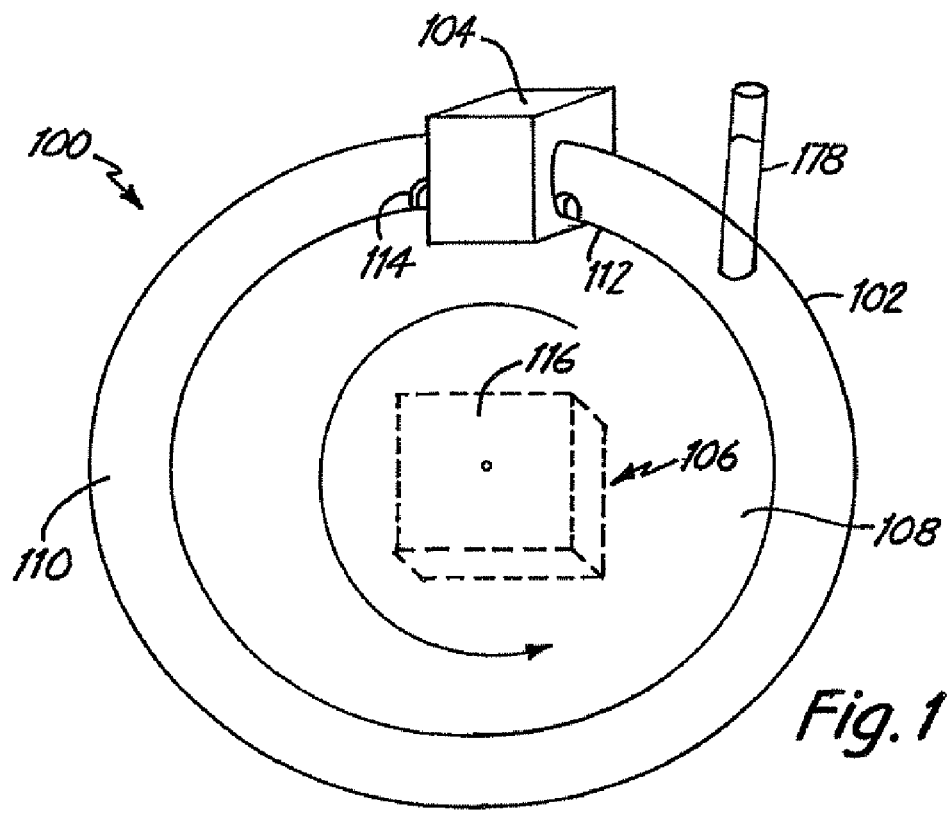
Fig.1
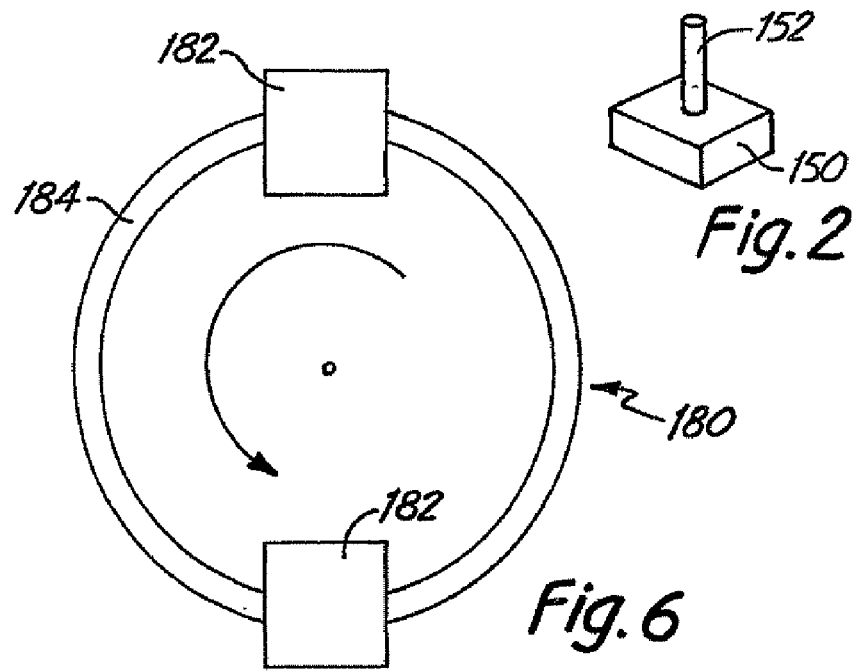
Fig.2
Fig.6

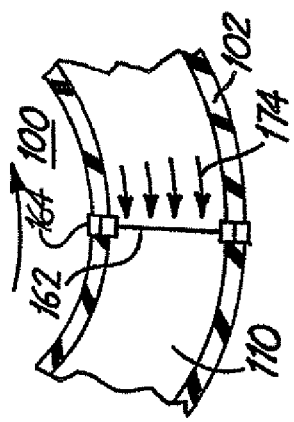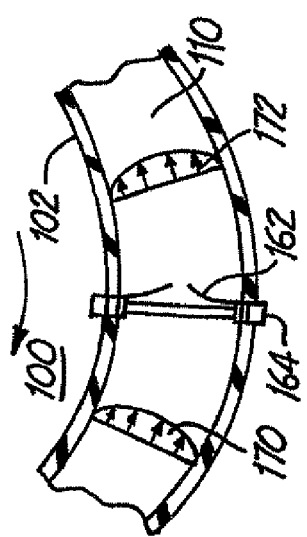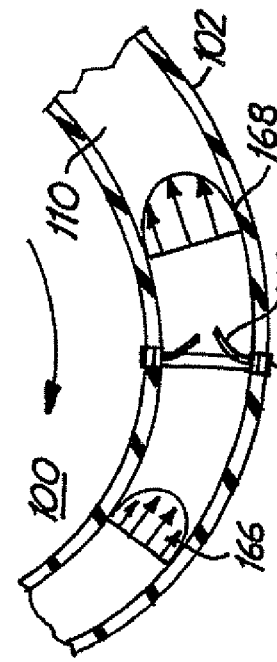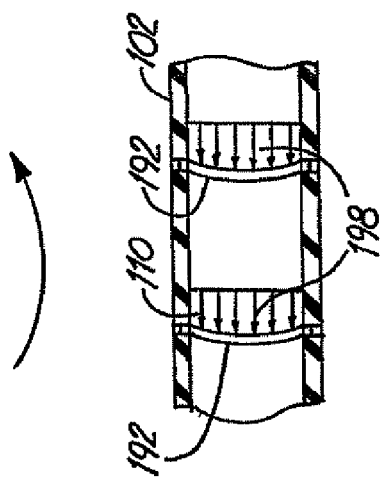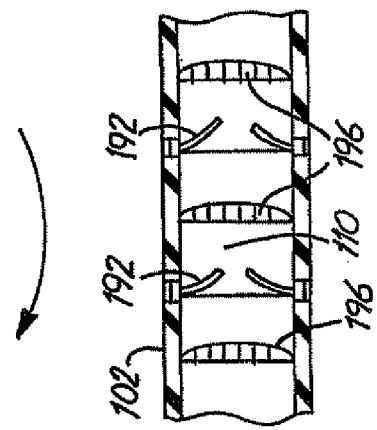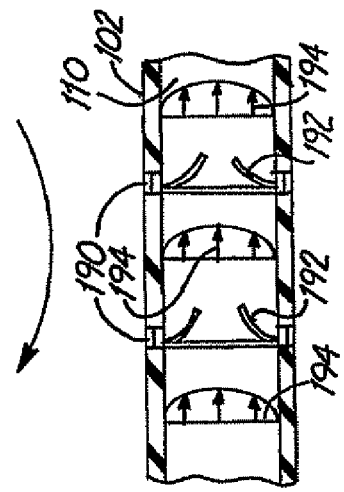

FLOW SYSTEM FOR MEDICAL DEVICE EVALUATION AND PRODUCTION

ACKNOWLEDGEMENT OF GOVERNMENT SUPPORT

This invention was made with United States Government support under Cooperative Agreement Number 70NANB9H3000 awarded by the National Institute of Standards and Technology (NIST). The United States Government has certain rights in the invention.

BACKGROUND OF THE INVENTION

The invention relates to a flow system/bioreactor that can be used for testing medical devices, such as heart valve prostheses, and/or producing medical devices. The flow system may be useful for maintaining viable cells and/or culturing cells. In particular, the invention relates to systems with a flow, preferably pulsed flow, of a fluid.

To design and/or produce medical devices that contact a patient's body fluids and/or tissues, it may be desirable to use a system that can simulate physiological conditions. The desired features of a particular testing or production system generally depend on the particular objectives. However, the flow system preferably simulates certain physiological conditions to provide mechanical and/or biological features of interest. In some circumstances, it is desirable to maintain and/or introduce viable cells that require suitable conditions to maintain their normal function.

Various medical devices have been designed particularly for contact with a patient's body fluids and/or tissues. This contact can be sufficiently long such that surface interactions between the medical device and the patient's fluids and/or tissues become significant. For example, the host interaction with the medical device can lead to degradation, such as calcification of the medical device. Relevant medical devices include, for example, catheters and, especially, prostheses.

Catheters include percutaneous devices that penetrate the skin to provide access to a body system. Prostheses, i.e., prosthetic devices, are used to repair or replace damaged or diseased organs, tissues and other structures in humans and animals. Implantable prostheses, such as heart valve prostheses, are generally biocompatible since they are typically implanted for extended periods of time.

Prostheses can be constructed from natural materials, such as tissue, synthetic materials or a combination thereof. Prostheses formed from purely synthetic materials, such as mechanical heart valve prostheses, can be manufactured, for example, from biocompatible metals, ceramics, carbon materials, such as graphite, polymers, such as polyester, and combinations thereof.

Mechanical heart valves can be manufactured with rigid occluders or leaflets that pivot to open and close the valve. Although mechanical heart valves with rigid pivoting occluders have the advantage of proven durability through decades of use, they are associated with blood clotting on or around the prosthetic valve. For this reason, patients with implanted mechanical heart valves remain on anticoagulants for as long as the valve remains implanted.

Heart valve prostheses can be constructed with flexible tissue leaflets or polymer leaflets. Prosthetic tissue heart valves can be derived from, for example, porcine heart valves or manufactured from other biological materials, such as bovine pericardium. Prosthetic heart valves made from biological materials generally have profile and surface characteristics that provide laminar blood flow. Therefore, intravascular clotting may be less likely to occur than with mechanical heart valves.

However, some prosthetic tissue heart valves are limited by a tendency to fail beginning about seven years following implantation. Calcification, i.e., the deposition of calcium salts, especially calcium phosphate (hydroxyapatite), appears to be a major cause of degeneration. Thus, tissue heart valves are generally used for older patients who experience less calcification and require the valve for shorter lengths of time. In addition, various approaches have been developed to reduce the effects of calcification, such that tissue heart valves will have greater durability. As these approaches achieve demonstrated long term effectiveness, tissue heart valves will find greater use.

A disadvantage of currently available tissue and polymer based prostheses is their inability to remodel. Long term durability may be affected by the lack of viable cells to populate the implanted substrate, to inhibit calcification and other forms of degeneration and to carry out maintenance functions. In addition, the presence of viable cells may result in improved hemodynamic performance and/or reduced thrombogenicity.

Prostheses generally are manufactured to last for significant periods of time with very high reliability. Therefore, in the development of prostheses, the prostheses may be subjected to suitable conditions to simulate in vivo function. Similarly, approximate physiological conditions may be significant for testing and/or preparation of prostheses since the prostheses may include viable cells or serve as an attachment and/or growth substrate for viable cells removed from their surroundings. Since natural biological conditions can be useful for the testing of certain prostheses and the preparation of other prostheses, it is desirable to have appropriate apparatuses to simulate natural biological conditions.

SUMMARY OF THE INVENTION

In a first aspect, the invention pertains to an apparatus comprising a medical device mount, fluid, and a conduit containing the fluid and the medical device mount. Generally, the conduit is mounted on an assembly that moves the conduit along with the medical device mount to induce motion of the fluid relative to the medical device mount.

In another aspect, the invention pertains to a method for inducing fluid flow. The method comprises moving a conduit containing a fluid and a medical device mount. The movement of the conduit induces a relative flow of fluid past the medical device mount. In some embodiments, a medical device is connected to the mount.

Furthermore, the invention pertains to an apparatus comprising a fluid and a conduit containing the fluid. The fluid comprises cells, and the conduit is mounted on an assembly that moves the conduit to induce relative motion of the fluid relative to the conduit.

In a further aspect, the invention pertains to an apparatus comprising a continuous flow pump connected to a conduit loop having multiple branch conduits downstream from the pump. The multiple branch conduits provide alternative paths over a section of the conduit loop. Each branch conduit has a valve controlling flow through the branch. In some embodiments, at least one branch comprises a medical device mount.

In addition, the invention pertains to a method of inducing flow, the method comprising generating flow with a continuous pump. The flow from the pump flows through a plurality branch channels in which flow into the branch channels is controlled by flow control valves. The flow control valves can induce pulsed flow within a branch by opening and closing to regulate flow into the branch.

BRIEF DESCRIPTION OF THE DRAWINGS

FIG. 1 is a schematic diagram of a flow system in which fluid motion is induced by rotation of a fluid-containing tube.

FIG. 2 is a schematic diagram of a drive system for the flow system of FIG. 1, in which the drive system incorporates a servo motor.

FIG. 3 is a schematic diagram indicating a relative counter-clockwise fluid flow within a clockwise rotating tube with a check valve.

FIG. 4 is a schematic diagram of the fluid flow within the rotating tube of FIG. 3 with a slower rotation rate.

FIG. 5 is a schematic diagram of the pressure exerted on the closed check valve within the rotating tube of FIG. 3 with a counter-clockwise rotation.

FIG. 6 is a schematic diagram of an embodiment of a flow system with two mounts for medical devices.

FIG. 7 is a schematic diagram indicating a relative counter-clockwise fluid flow within a clockwise rotating tube holding two check valves.

FIG. 8 is a schematic diagram of the flow within the rotating tube of FIG. 7 with a slower rotation rate.

FIG. 9 is a schematic diagram of the pressure exerted against the check valves within the rotating tube of FIG. 7 with a counter-clockwise rotation.

DETAILED DESCRIPTION OF THE ILLUSTRATIVE EMBODIMENTS

Figure 10:
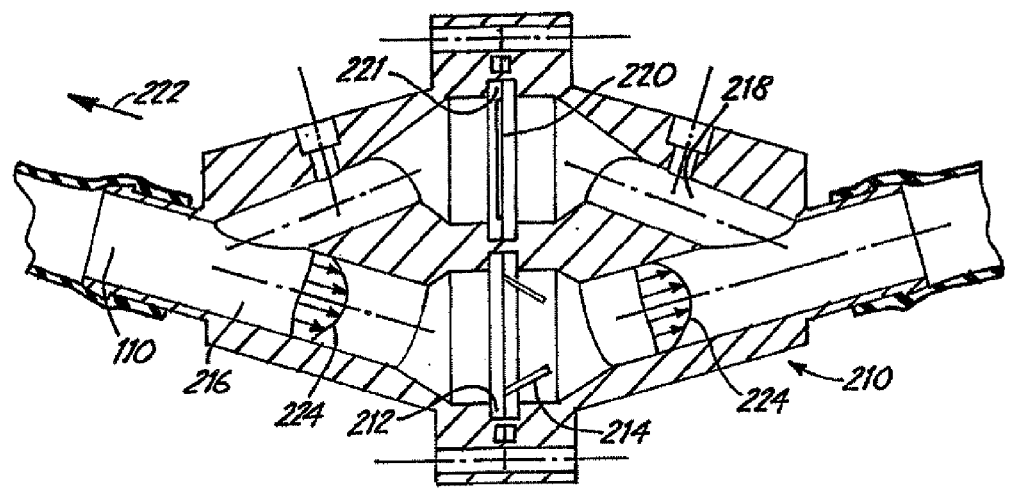
FIG. 10 is a sectional view of a mount for a check valve, the section being taken through the center of the valve, in which the mount has a side channel and in which the flow due to clock-wise rotation is indicated schematically.

Improved flow systems/bioreactors produce flow conditions such that medical devices can be tested and/or produced under pulsed flow conditions and/or such that viable cells can be maintained or cultured with less damage. The flow systems can be used to more closely approximate natural biological conditions in which pulsed flow circulates fluid. Pulsed flow is induced in the flow systems without use of a pump that directly applies pulsatile forces to the fluid. In place of standard pulsed pumps in the flow systems/bioreactors, continuous flow pumps or physical movements of fluid-containing tubes as described herein are used to induce pulsed fluid flow. While standard pulsed pumps tend to damage cells due to the forces applied by the pumps, the alternative approaches to induce pulsed flow described herein reduce or eliminate corresponding cell damage.

In some preferred embodiments, a medical device is placed within a conduit that is physically moved to initiate fluid flow relative to the medical device. Periodically reversing the motion of the conduit creates the pulsed flow of the fluid. In alternative preferred embodiments, pulsed flow is created with a continuous pump by alternatively closing valves leading to branched flow paths. Appropriately selecting a sequence for opening and closing the valves results in pulsed fluid flow.

The improved flow systems are particularly useful for circulating blood, cell culture medium or other fluids containing viable cells. For example, by circulating fluid containing viable cells, the flow systems can be used for seeding biocompatible materials with viable cells. Thus, the flow systems can be used to produce prostheses with associated cells.

Since the conditions in the flow systems can be adjusted to mimic the conditions in a patient's cardiovascular system, the flow systems can also be used to test and evaluate cell attachment and proliferation in association with a prosthesis or cell culture support matrix. The cell attachment and proliferation approximates the expected response following implantation of the prosthesis within a patient. Similarly, the flow systems can be used for various testing procedures for medical devices under a wide range of conditions, such as physiologically representative conditions. The interaction of a medical device with fluids under pulsed flow, including fluids containing viable cells, can be examined. Pulsed fluid flow is desired because pumping of the heart creates pulsed fluid motion within the cardiovascular system. Testing of the medical device can investigate, for example, fluid dynamics, thrombogenicity, cell recruitment/colonization and/or bacterial/fungal colonization. The evaluation can take place over a wide range of conditions that can be achieved by varying, for example, flow rate, pulse rate, pressure, forward and reverse flow duration, temperature and pH.

In general, relevant medical devices are prostheses that are formed to mimic a corresponding structure within the body. The prostheses can be used to replace the corresponding native structures. Other prostheses are used to repair damaged or diseased native structures. The medical devices can be prosthetic devices or components suitable for long term implantation within a recipient patient. Generally, the patient is an animal, preferably a mammal, such as a human. Prostheses include tissue engineered organs that are not implanted, such as hepatocytes that are exposed to a patient's blood flow externally to extend the life of a patient experiencing acute liver failure. Other suitable medical devices include, for example, percutaneous devices, such as catheters or components thereof, that are inserted into a patient's blood flow during use. In addition, suitable medical devices include cell culture support matrices.

The flow systems described herein preferably produce pulsed flow without the use of a pulsatile pump that directly pulses the fluid. In some embodiments, the pulsed flow is induced by other mechanical manipulations without directly applying a localized pulsed driving force against the fluid at a specific pump location within the flow system. In some embodiments, a flow of fluid through the system is obtained by moving the system or a portion thereof. For example, a closed loop, e.g., circular, conduit containing fluid can be rotated about its center. A differential in the relative velocity between the conduit and the fluid will result, thereby creating relative fluid flow past a medical device mounted in the conduit. By placing a check valve, which can be a valved medical device, in the conduit, the flow of fluid past the medical device can be stopped by reversing the direction of conduit rotation. In this manner, pulsed fluid flow past the medical device can be obtained.

In other embodiments, a continuous pump is used to initiate fluid flow through a conduit loop. A portion of the conduit loop may include multiple alternative branches for flow. Each branch of the conduit includes a valve which controls flow into the particular branch. Preferred flow control valves include pinch clamps. One or more medical devices are placed within one or more of the branches. In preferred embodiments, at least one of the branches does not include a medical device. Pulsed flow at the medical devices is produced by alternating opening and closing of the flow control valves.

Fluid containing viable cells residing within the flow system can be blood, culture medium or other fluids/liquids. Since it has a viscosity and composition corresponding to in vivo conditions, blood can be used to mimic conditions within the body more closely. The flow systems can include components to perform oxygenation, nutrient introduction, cell introduction and other manipulations. Maintenance of fluid conditions, especially with respect to oxygen and nutrients, allows for longer term evaluations under near physiological conditions and for the maintenance of cell viability and cell function for extended periods of time.

The medical device can include synthetic materials and/or tissue materials. When the fluid contains viable cells, the flow system can be used to evaluate the interaction of cells and medical devices under physiologically representative conditions. The flow system generally remains sterile during use. The flow system can be used to evaluate medical device performance with pulsed flow similar to in vivo conditions with a fluid that does not include viable cells.

In other embodiments, the flow system can be used to evaluate cell colonization of a medical device. Alternatively, if the prosthesis has viable cells initially, the flow system can be used to evaluate the continued function of the cells, such as proliferation, and/or the association of different cell types following exposure to the cells in the circulating fluid. If the prosthesis does not have viable cells initially, the flow system can be used to evaluate association of viable cells of one or more types with the prosthesis.

Similarly, in other embodiments, the flow system can be used to examine the properties of biocompatible materials. The biocompatible material can be held within the flow system to evaluate the continued function of the cells, such as proliferation, and/or the association of different cell types following exposure to the circulating fluid. The structure within the flow system will be referred to broadly as a medical device to cover the embodiments in which the structure within the flow system is a prosthesis or catheter formed from synthetic materials and/or a tissue, as well as other biocompatible materials placed within the system for any purpose. In other embodiments, the flow system can be used to culture cells, for example, under physiologically representative conditions.

Flow Apparatus

The flow apparatus provides for improved pulsed flow without the use of a pump applying localized pulsatile driving forces on the fluid, such as a peristaltic pump or diaphragm pump. Thus, forces applied by pulsed pumps that can damage viable cells are eliminated. Since pulsed fluid motion can mimic motion induced by a pumping heart, pulsed motion is desired, particularly to produce or to test the performance of valved prostheses, especially heart valve prostheses, that function as check valves.

In some embodiments that contain check valves, such as valved prostheses, pulsed fluid motion is induced by movement of the flow system or a portion thereof in one direction and followed by movement in the reverse direction. In other embodiments which utilize non-pulsatile pumps, pulsed fluid motion is created by continuously pumping fluid in a conduit loop and selectively opening and closing valves leading to multiple branches in the flow loop. If the valves are appropriately opened and closed, flow within the branches has pulsed character.

Embodiments With Motion of Portions of the System

Motion of a conduit containing fluid can result in relative difference in movement between the conduit and the fluid. This occurs as the fluid remains stationary while the conduit travels past it. The placement of an optional check valve in the conduit can allow more control over the characteristics of the pulsed fluid flow relative to the conduit. The motion of the conduit can be, for example, rotational or linear.

A first embodiment based on rotational motion is shown schematically in FIG. 1. Pulsed flow apparatus 100 includes a tube 102, a medical device mount 104 and a drive system 106. Tube 102 connects to medical device mount to form a closed loop for fluid flow.

Tube 102 can be formed from a nontoxic material that is inert with respect to fluid 110. Suitable materials include, for example, metals, such as stainless steel, and biocompatible polymers, such as polysilicates, polyurethanes, polyethylene, polyvinylchloride and combinations thereof. Suitable tubing 102 includes silicon tubing.

Mount 104 can have any reasonable structure based on the structure of the medical device. Generally, the mount releasably supports the medical device, such that the medical device can be subsequently removed from the mount without damage. For example, if the medical device is a tissue construct, mount 104 can be a platform with clips or other holding members that hold the tissue construct at a selected angle in the fluid flow. In preferred embodiments, the mount does not change the diameter of the flow and does not influence the flow conditions in a deleterious or disadvantageous way. Reducing disruptions in the flow correspondingly reduces cell damage.

In preferred embodiments, the medical device is a valved prosthesis, such as a mechanical valve, a polymer valve or a tissue-based valve. For prosthetic valves, mount 104 generally holds the valve and makes a seal such that fluid flows through the valve, preventing flow around the valve. Pressure transducers 112, 114 can be placed in the fluid flow adjacent to the medical device held by mount 104 to measure the pressure differential across the medical device.

Whether or not the medical device includes a valve, the flow system can include a check valve to generate desired flow properties. If the medical device includes a valve, such as a valved prosthesis, the medical device itself, properly mounted, can function as the check valve to generate the desired flow. In general, the flow system can include a plurality of medical device mounts and/or a plurality of check valves, of which all, a portion or none are medical devices. Below, check valves affecting flow are described in the context of fluid flow within the flow system. These check valves may or may not be medical devices, such as valved prostheses. If the check valve is a medical device, the check valve mount also functions as a medical device mount.

Drive system 106 can include various designs capable of rotating tubing 102 and mount 104. In one embodiment, tubing 102 and mount 104 are placed on a platform 108, such as a turntable. Rotation unit 116 rotates turntable 108. Rotation unit 116 can include, for example, a servo motor or pneumatic drive.

In preferred embodiments, a servo motor can be used in rotation unit 116. Referring to FIG. 2, servo motor 150 rotates drive coupler 152 to drive platform 108. Suitable servo motors include, for example, Parker Motion and Control Model DR5070, available from Parker Hannifin Corp., Cleveland, Ohio.

In an alternative embodiment, rotation unit 116 includes a rotating drive coupler 152 connected to a linear actuator. Movement of the linear actuator rotates drive coupler 152. Movement of the linear actuator is controlled with compressed air from compressed air source, such as an air tank or compressor.

As shown in a fragmented sectional view in FIG. 3, pulsed flow can be established by repeatedly rotating a generally circular flow system 100 about its center and then stopping the rotation. At the onset of rotation, components of flow system 100 move relative to fluid 110. Thus, fluid 110 moves past any component, including a medical device, mounted within flow system 100. By repeatedly starting and stopping rotation, fluid flow relative to flow system 100 is pulsed. By repeatedly starting and reversing rotation, flow can be repeatedly reversed relative to rotating components of flow system 100. Thus, a medical device mounted within flow system 100 can be subjected to forward fluid flow, no fluid flow or reverse fluid flow. The rate and direction of relative flow can be adjusted by controlling the angular velocity of flow system 100 and the direction of rotation.

If it is desired to establish a pulsed flow without subjecting a medical device within flow system 100 to a reverse flow, a check valve 162 can be placed within flow system 100, as shown in a fragmentary sectional view in FIG. 3. Check valve mount 164 which is attached to tube 102 holds check valve 162.

When selecting a check valve, preferred valves reduce disruptions in the diameter of the flow stream. In general, a low amount of friction and drag between fluid 110 and components of flow system 100 is desired. Suitable check valves include valved prostheses, such as heart valve prostheses, such that the medical device itself functions as the check valve.

As configured in FIG. 3, when flow system 100 rotates in the direction shown, check valve 162 opens, and the walls of tubing 102 are moved past fluid 110 establishing a relative velocity profile 166, 168. Referring to FIG. 4, as the duration of the rotation increases, the relative velocity profiles 170, 172 between the inner wall of tubing 102 and fluid 110 are diminished, as fluid begins to move in the direction of rotation due to friction. The magnitude of change in relative velocity over time depends on several factors including, for example, the angular velocity of rotation, the duration of rotation, tubing diameter, the surface properties of the inner wall of tubing 102, viscosity of the fluid, and the shape and orientation of the medical device within flow system 100.

When rotation is reversed, as shown in FIG. 5, the fluid mass exerts a force 174 on check valve 162 causing it to close. When check valve 162 closes, check valve 162 drives fluid 110 in the direction of rotation. The relative velocity profile between fluid 110 and tubing 102 diminishes to zero and flow ceases. Thus, repeatedly alternating direction of rotation results in pulsed flow.

Force applied to valved prosthesis 162 when it is in a closed position is indicated schematically with force profile vectors 174. The amount of force acting upon the closed valved prosthesis is a function of the cross sectional surface area of the closed valved prosthesis normal to the plane in which the flow system resides, the mass of fluid 110 acting upon the valve, and the angular velocity of the flow system rotation.

The rate of flow and the direction of relative flow are controlled by the angular velocity of flow system 100. With a system having an overall diameter of about 18 inches (46 cm) and a tubing diameter of about ¾ inch (1.91 cm), the production of an average flow rate through the check valve of 4 liters/minute at a pulse rate of 60 beats/minute, in which the valve is open for fifty percent of a complete cycle, requires a rotational angle for a single pulse of about 75°. The direction of rotation oscillates between the forward and reverse direction for each cycle, opening and closing the check valve, which can be a valved prosthesis, for the desired time interval.

It may be desirable to control the pressure of fluid residing in flow system 100. The base pressure over atmospheric pressure can be established by simply adding a tube 178 (FIG. 1) containing fluid to flow system 100 and orienting the tube at a height above flow system 100. The pressure of fluid 110 is dictated by the head height of fluid 110 residing within tube 178. If the desired pressure requires a height of tubing that is impractical, the gas space residing above the fluid 110 can be compressed with a syringe, thumb screw or other device that can be used to establish and maintain the desired gas pressure. In the event that one does not want fluid 110 to directly contact gas, a membrane diaphragm can be used to separate the gas space from fluid 110. In other embodiments, the system is placed in a controlled pressure chamber at a desired pressure.

Total fluid volume of the flow system can be scaled up by increasing tubing diameter and/or length. The total volume of the system is preferably less than about 1 liter, preferably less than about 850 milliliters (ml), more preferably from about 400 ml to about 750 ml, and even more preferably about 400 ml to about 500 ml (presently the maximum allowable volume of whole blood collected from a single human donor, hereafter referred to as one unit of blood). Using tubing with an inner diameter of about ¾ inch (1.91 cm), the tubing has a volume of about 87 ml per linear foot (2.85 ml/cm). If the flow system is configured with check valves, an allowance for extra volume within the medical device mounts should be made. Thus, to achieve a system volume of about 500 ml, about 2.5 feet (76.2 cm) to about 3.5 feet (106.7 cm) of tubing can be used for a system having two medical device mounts.

A single pulsed flow system can include a plurality of medical device mounts. Pulsed flow can be established with or without a check valve, as previously described. Referring to FIG. 6, a pulsed flow system 180 has two medical device mounts 182 connected to a single loop of tubing 184 in a roughly symmetric configuration. More than two medical device mounts can be included, and the mounts can be placed adjacent, symmetrically or any other desired configuration within a loop of tubing. However, if the mounts are intended to hold a valved prosthesis and an objective is to expose each valved prosthesis to similar conditions, such as the force exerted upon the valve leaflets when they are in the closed position, symmetric placement of the mounts is preferred. By symmetric placement, each valved prosthesis is exposed to an equal mass of fluid when the flow system reverses rotational direction and the leaflets of the valved prosthesis are closed. Regardless of the medical device held by mounts 182, symmetric placement will tend to balance the angular forces during rotation.

Pulsed flow within a flow system having multiple check valves, such as valved prostheses, is analogous to flow with a single check valve. For example, clockwise rotation with two check valves is shown in the fragmentary sectional view of FIG. 7. Check valve mounts 190 secure valved prostheses 192 within tube 102. When tube 102 is rotated in a clockwise direction, as indicated by the arrow, a flow is established due to the difference in relative velocity between the inner wall of tube 102 and fluid 110 that is shown schematically with flow vectors 194. The flow opens valved prostheses 192.

As rotational velocity is reduced or when friction between the inner wall of tube 102 and fluid 110 begins to drag fluid 110 in the direction of rotation, the relative velocity profile between fluid 110 and the inner wall of tubing 102 is also reduced. The diminished relative velocity profile is indicated schematically in FIG. 8 by relative velocity profile vectors 196.

Referring to FIG. 9, when direction of rotation is reversed, valved prostheses 192 close as the mass of fluid 110 acts upon the leaflets. Force applied to valved prostheses 192 when they are in a closed position is indicated schematically with force profile vectors 198. The amount of force acting upon the closed valved prostheses is a function of the cross sectional surface area of the closed valved prostheses normal to the plane in which the flow system resides, the mass of fluid 110 acting upon the valve, and the angular velocity of the flow system rotation.

Figure 11:
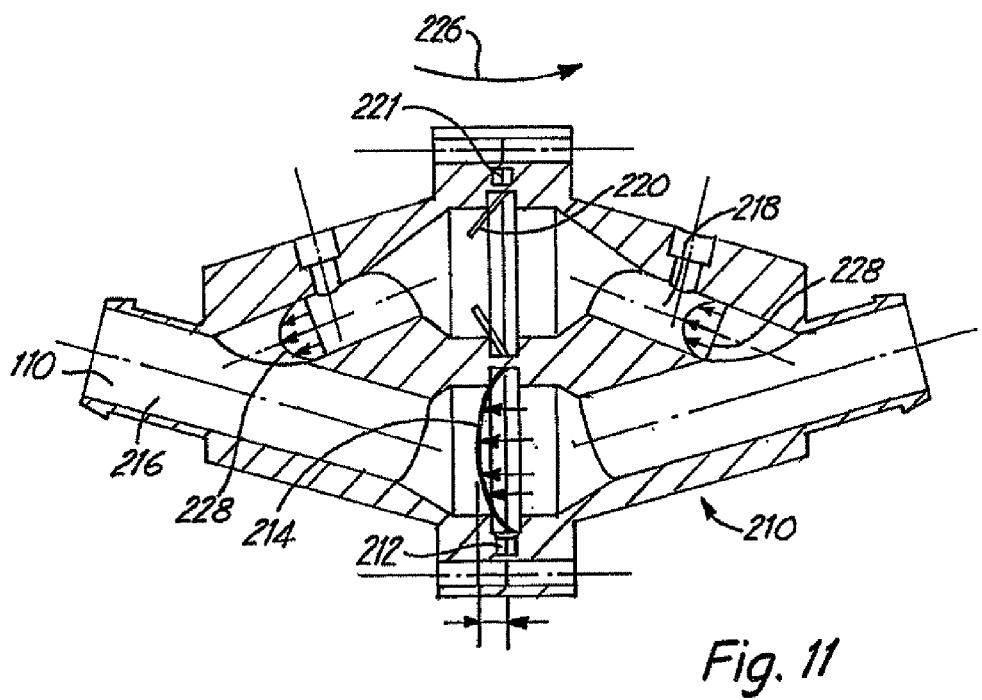
FIG. 11 is a sectional view of the mount of FIG. 10 in which the flow due to counter clock-wise rotation is shown schematically.

An alternative embodiment of a valve mount is shown in a fragmentary cross section in FIGS. 10 and 11. This embodiment provides an alternative flow path that allows more control of the force applied to the leaflets of the valved prosthesis. Valve holder block 210 includes a first valve mount 212 holding a first check valve 214 within main channel 216. In preferred embodiments, check valve 214 can be a valved prosthesis. Bypass channel 218 optionally can have a second check valve 220 that is mounted with valve mount 221 in an opposite configuration to check valve 214 such that check valve 220 is open when check valve 214 is closed and vice versa. Thus, bypass channel 218 provides a means to allow bypass flow around main channel 216 when check valve 214 is closed. The housing of valve holder block 210 can be made from any biocompatible material, preferably transparent, for example, polycarbonate, polystyrene and/or acrylic polymers, such that the valve is visible during operation of the flow system.

Care should be taken to insure that valve mount 212 is appropriately sealed in a manner that prevents fluid flow around the outer perimeter of check valve 214 or leakage outside the flow system. Use of o-rings, adhesives, gaskets, sonic welds and other forms of liquid tight seals, including those commonly used in the art, are acceptable. As with all components in contact with the fluid in the flow system, biocompatible materials are desirable when viable cells reside within the flow system. Flow channels through valve holder block 210 should be designed such that they do not alter the generally circular flow path since deformity of the flow path contour can disrupt the flow. For example, when motion is rotational, flow through main channel 216 should conform as much as possible to the circumference of the flow system. While generally circular flow paths are preferred, some embodiments with oval flow paths can be used.

As shown in FIG. 10, the flow system is rotating clockwise as indicated by arrow 222. A flow field results from the relative velocity profile 224 that is established by the rotation. Check valve 214 opens due to the mass of fluid 110 exerted during flow. Similarly, check valve 220 closes during clockwise rotation due to the mass of fluid 110 acting upon it. Referring to FIG. 11, the system is rotating in a counter clockwise direction indicated by arrow 226. As a result, a relative velocity profile 228 is established in a direction opposite to the direction of the flow shown in FIG. 10. Check valve 214 closes in response to the mass of fluid 110 acting upon the leaflets, and check valve 220 opens due to the mass of fluid acting upon it. By allowing fluid to pass through check valve 220, the mass of fluid exerting a force on the leaflets of the check valve 214 is reduced. In this manner, the force applied to the leaflets can be more accurately controlled by the design of bypass channel 218. Factors that affect flow through bypass channel 218 include the diameter of bypass channel 218, the angle between bypass channel 218 and flow channel 216, and the surface finish of bypass channel 218. In general, a larger diameter of bypass channel 218 will diminish the force exerted on check valve 214. Alternatively, a reduced diameter of channel 218 will increase the force exerted on check valve 214.

In the case where multiple check valves exist in a flow system, some valves may remain open if one valve closes first and the flow system is not configured to allow the mass of the fluid in the flow system to distribute to all of the valves. If this occurs, once one valve is closed, relative flow of the fluid is terminated, and no force is exerted on the remaining check valves. Valve holder block 210 in FIGS. 10 and 11 can be beneficial for preventing the circumstances in which only one of a plurality of valves closes. In particular, fluid flow through bypass channel 218 of valve holder block 210 enables continued fluid flow. Thus, as the mass of fluid is distributed throughout the flow system, closing force is distributed to all the check valves.

Figure 12:
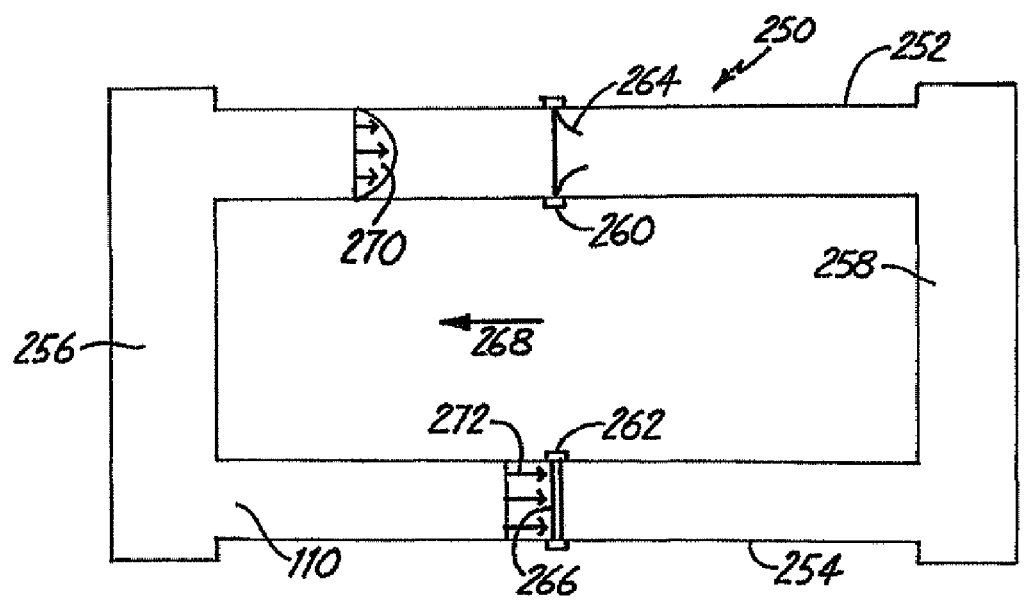
FIG. 12 is a sectional view of a flow system wherein flow is induced by translation from right-to-left of a fluid-containing tube, the system holding two check valves, and the section being taken through the center of the valve mounts.
Figure 13:
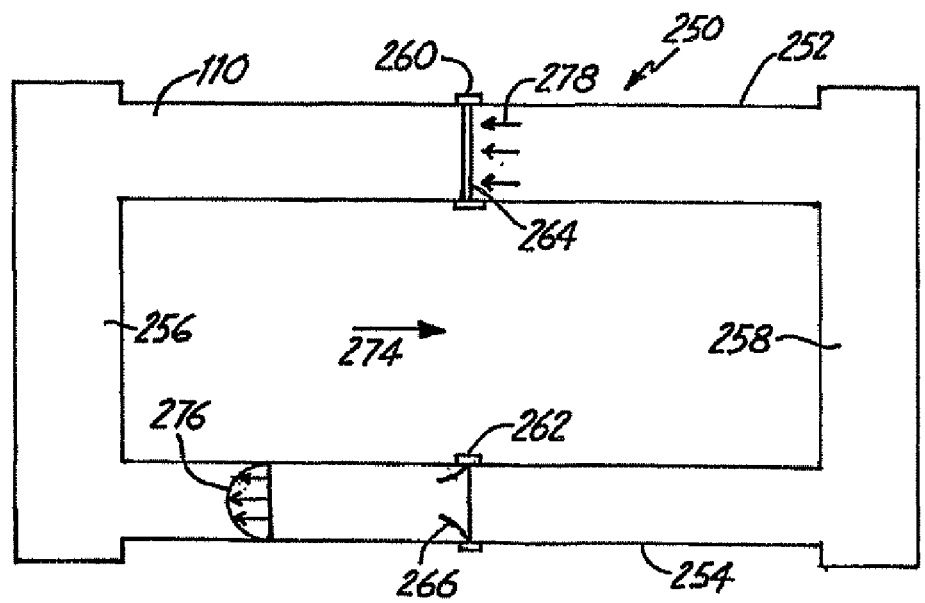
FIG. 13 is a sectional view of the system of FIG. 12 with translation from left-to-right.

While rotation is a convenient motion to initiate flow, other motions can be similarly effective. For example, translational motion can be used to induce flow while reducing angular forces such as coriolis forces and centrifugal forces within the fluid. A suitable flow system holding two check valves/valved prostheses is shown in FIGS. 12 and 13. Flow system 250 includes tubes 252, 254 that meet at reservoirs 256, 258. Tubes 252, 254 each include a medical device mount 260, 262. In some embodiments, the medical device is a valved prosthesis. As shown in FIGS. 12 and 13, valved prostheses 264, 266 are held by medical device mounts 260, 262, respectively.

If contact of fluid 110 with gas is disadvantageous, reservoirs 256, 258 can be any suitable flexible or elastic biocompatible container. It may be desirable to select a material with a low moisture vapor transmission rate to avoid evaporation and potential osmolarity changes in fluid 110. Consideration of oxygen and carbon dioxide permeability may be relevant depending on the methods used to control the oxygen tension and pH of fluid 110. As fluid 110 enters and exits the flexible/elastic reservoirs, they expand and contract to accommodate the changing volume. In this fashion, fluid 110 does not come in direct contact with gas. If contact of fluid 110 with gas is not disadvantageous, reservoirs 256, 258 should have empty volumes at heights above the tops of tubes 252, 254. In addition, each reservoir preferably has enough excess volume of fluid above the tops of tubes 252, 254 that flow results in a shift of fluid from one reservoir to the other without gas entering into tubes 252, 254. It is preferable to limit agitation of the fluid to avoid foaming and/or cell damage. Thus, the design should attempt to maintain laminar flow of fluid 110 when designing reservoirs 256, 258 and the interface of reservoirs 256, 258 with tubes 252, 254 and of tubes 256, 258 with medical device mounts 260, 262.

To introduce the translational motion, any suitable drive system can be used. For example, the system can be mounted on a platform that is placed on a shaker table or the like. As shown in FIG. 12 by arrow 268, flow system 250 is being translated from right to left. This motion induces a flow in tube 252 as indicated by relative velocity profile 270. The flow opens valve 264 and closes valve 266 as the mass of fluid 110 exerts a force on the leaflets indicated schematically with force vectors 272. Reservoir 258 expands in fluid volume in direct proportion to the depletion of fluid volume in reservoir 256.

Translational motion is reversed in FIG. 13 from left to right, as shown by arrow 274. This motion induces a flow in tube 254 as indicated by the relative velocity profile 276. This flow opens valve 266 and closes valve 264 as the mass of fluid 110 exerts a force on the leaflets indicated schematically with force vectors 278. Reservoir 256 expands in fluid volume in direct proportion to the depletion of fluid volume in reservoir 258.

Other embodiments incorporate desirable features of the rotating and translating embodiments described above. In these embodiments, two opposite sections are simultaneously translated in opposite directions. A reservoir of fluid is unnecessary. The tubes are necessarily very flexible such that the tube winds around two ends of an oval formed by the tube. Referring to FIGS. 14-17, flow system 280 includes flexible, biocompatible tubing 282, such as platinum cured silicone tubing, holding fluid 110. Tubing 282 revolves around rollers 284, 286, although other constructions can be similarly used to guide tubing 282.

Figure 14:
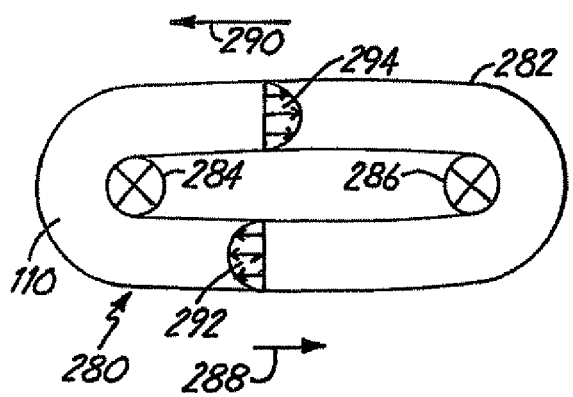
FIG. 14 is a schematic diagram of an alternative embodiment of a flow system involving revolution of a flexible tubing by moving opposite sides of the tubing in opposite directions.
Figure 15:
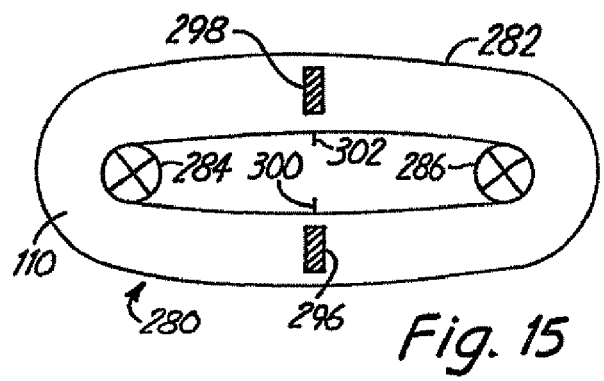
FIG. 15 is a schematic diagram of the flow system of FIG. 14 with marking on the tubing and portions of fluid identified.
Figure 16:
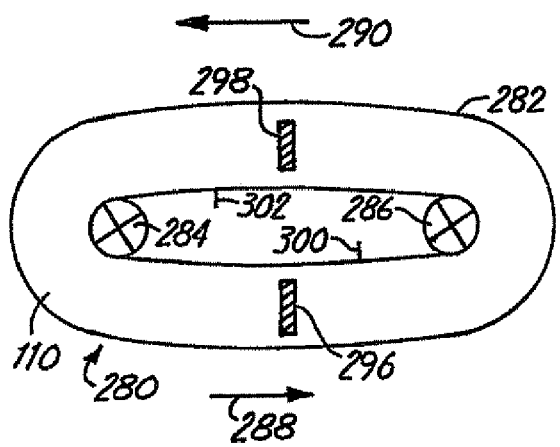
FIG. 16 is a schematic diagram of the flow system of FIG. 14 following translation of opposite sides of the tubing as indicated by arrows to revolve the tubing around rollers.

Referring to FIG. 14, simultaneous movement of tubing 282 depicted in the bottom portion of the figure as indicated by arrow 288 and the upper portion of tubing 282 as indicated by arrow 290 creates at the onset of motion a flow with velocity profiles 292, 294. Referring to FIG. 15, two portions of fluid 296, 298 are depicted along with two marked sections of tubing wall 300, 302. Referring to FIG. 16, upon rapid movement of the opposite sections of tubing 282 as indicated by arrows 288, 290, fluid portions 296, 298 remain relatively stationary while tubing 282 moves, as indicated by the positions of marked tubing wall 300, 302. At a high translational velocity of tubing 282, there is little drag between tubing 282 and fluid 110. Thus, relative motion is established between the fluid and tubing.

Figure 17:
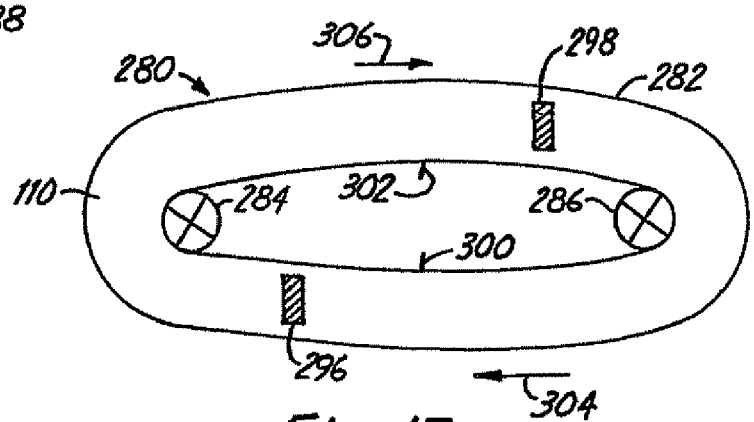
FIG. 17 is a schematic diagram of the flow system of FIG. 16 following slow translational motion with fluid drag in the opposite direction of the translation indicated in FIG. 16.

Referring to FIG. 17, following slow translational motion in the opposite direction as indicated by arrows 304, 306, fluid portions 296, 298 translate as indicated to maintain roughly the same relative position between fluid portions 296, 298 and marked tubing wall 300, 302. At slow translational motions of tubing 282, there should be considerable drag between fluid 110 and tubing 282. Repeated translational cycling in this manner induces pulsed flow. By depicting fluid portions 296, 298 as indicated in FIGS. 15-17, it is assumed that there is little mixing or diffusion, however the basic concepts illustrated are unchanged by diffusion and/or mixing of the fluid.

Figure 18:
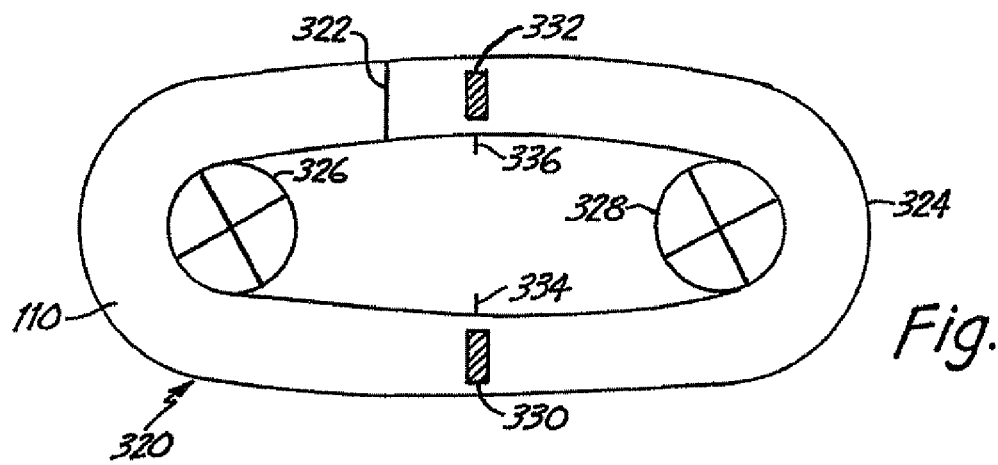
FIG. 18 is a schematic diagram of the flow system in FIG. 14 with a check valve included within the tubing.
Figure 19:
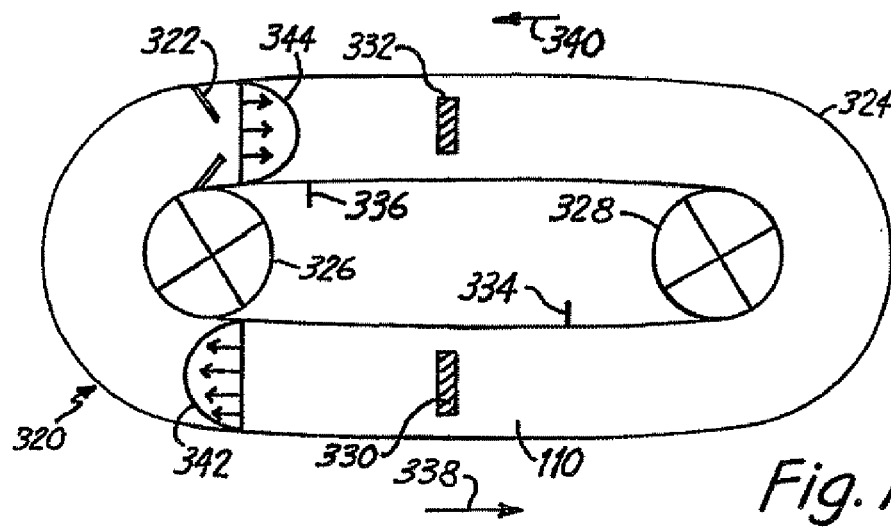
FIG. 19 is a schematic diagram of the flow system of FIG. 18 with translation of opposite sides of the tubing in the directions indicated by the arrows.
Figure 20:
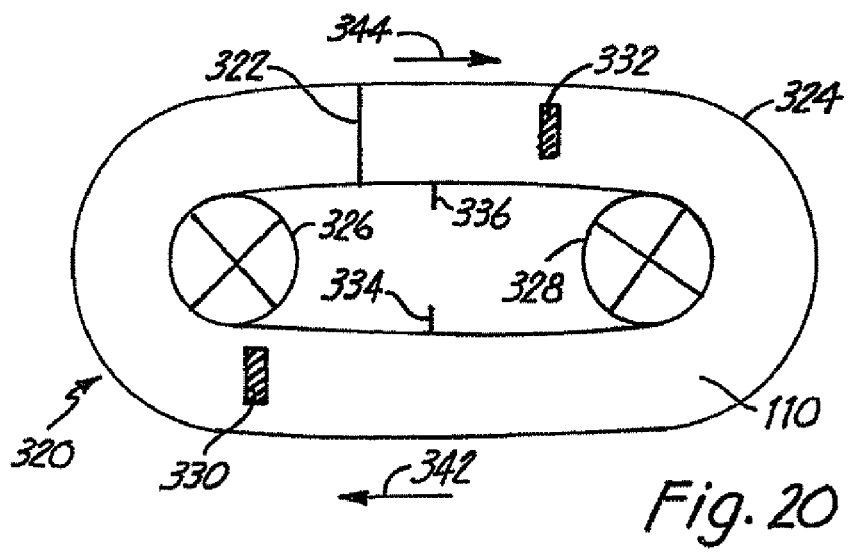
FIG. 20 is a schematic diagram of the flow system of FIG. 19 following reverse translational motion of opposite sides of the tubing as indicated by arrows.

Referring to FIGS. 18-20, flow system 320 includes a check valve 322 within biocompatible, flexible tubing 324 holding fluid 110. Tubing 324 is held in position by rollers 326, 328. In FIG. 18, fluid portions 330, 332 and marked tubing wall positions 334, 336 are shown. Flow system 320 is shown in FIG. 19 following rapid translation of opposite sections of tubing 324 as indicated by arrows 338, 340. With rapid translation, there is little drag between tubing 324 and fluid 110, such that fluid portions 330 and 332 remain stationary. Check valve 322 is translated along with tubing 324. Translational motion indicated by arrows 338, 340 establishes relative flow indicated by velocity profiles 342, 344. Referring to FIG. 20, flow system 320 is shown following translation of the opposite sections of tubing 324 in the directions indicated by arrows 342, 344 starting from the orientation indicated in FIG. 19. As the mass of fluid 110 is exerted upon check valve 322, check valve 322 closes, thereby driving fluid 110, and fluid portions 330, 332, in the direction of rotation. Marked positions of tubing 334, 336 move similarly in the directions of arrows 342, 344. In this example, fluid 110 has made a net movement in a clockwise direction after one cycle. Repeated translational cycling in this manner induces pulsed flow. More than one check valve can reside in the flow system. In this case, the use of a valve mount allowing bypass flow, such as the mount shown in FIG. 10, enables multiple valves to close properly, as discussed above with respect to FIGS. 10 and 11.

In the embodiments above, the oxygen content of the fluid within the system can be maintained by constructing tubing 102, from a gas permeable polymer. Suitable tubing material includes, for example, platinum cured silicone tubing, which is available from Barnant Company, Barrington, Ill. The system can be placed within a controlled environment chamber. The oxygen partial pressure in the controlled environment chamber is maintained at an appropriate value to keep the fluid residing within tube 102 oxygenated at the desired level. Similarly, carbon dioxide can permeate through the tubing for the control of pH. For embodiments with viable cells present, it generally is desirable to control the pH of the fluid between about 6.0 and about 9.0, preferably near physiological values from about 7.2 to about 7.6 pH unit by varying the concentration of $CO_2$. The gas within the controlled environment chamber can be maintained at desired composition and pressure.

Figure 21:
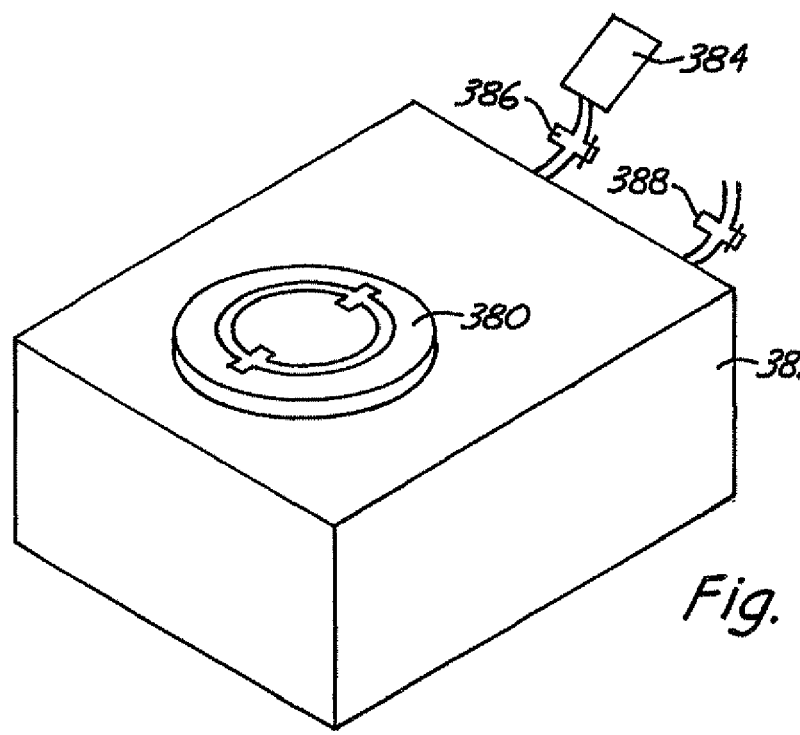
FIG. 21 is a schematic diagram of a flow system within a controlled environment chamber.

Such an embodiment is shown schematically in FIG. 21. Flow system 380 is located within controlled environment chamber 382. Controlled environment chamber 382 is connected to a gas source 384. Flow from gas source 384 into controlled environment chamber 382 is controlled by gas inlet valve 386. Gas is vented from controlled environment chamber 382 through gas outlet valve 388. To maintain a desired gas mix in controlled environment chamber 382, gas is supplied by gas source 384, and waste gas is removed through valve 388. The temperature in controlled environment chamber 382 can also be maintained within a desired range.

Alternatively, oxygenation can be performed using a gas exchange system or by placing a gas exchange apparatus in series with a fluid exchange apparatus. In addition, various heating/cooling arrangements, such as flowing the fluid through a heat exchanger, can be used to maintain flow system at a desired temperature. Generally, the system can be designed to operate over a temperature range, for example, from about 4° C. to about 42° C. In embodiments simulating physiological conditions, the temperature is set to a value between about 35.0° C. and about 38.0° C. with a tolerance of about 0.5° C.

To replenish or exchange fluids within flow system 100, a fluid exchange system can be attached to tube 102. Preferably, the fluid exchange system is stationary and does not rotate or translate with tube 102. Having a stationary fluid exchange system provides for greater design options.

Figure 22:
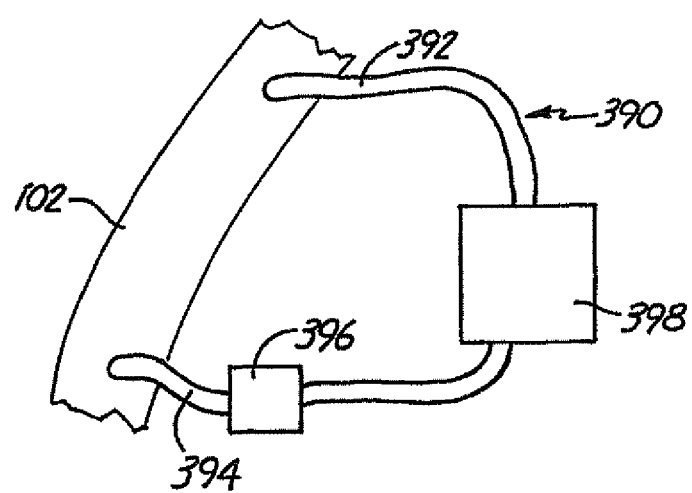
FIG. 22 is a schematic diagram of a fluid exchange apparatus connected to a flow system.

In one embodiment shown in FIG. 22, fluid exchange system 390 is connected to tube 102 through flexible tubing 392, 394. Fluid exchange system 390 includes a pump 396 and fluid exchange apparatus 398. Pump 396 maintains a flow from tube 102 through fluid exchange system 390 without disrupting the pulsed flow in tube 102. As long as the connection between the fluid exchange system and tube 102 has a suitable flexible component, there is no difficulty in having a stationary fluid exchange system connected to the moving flow system.

Figure 23:
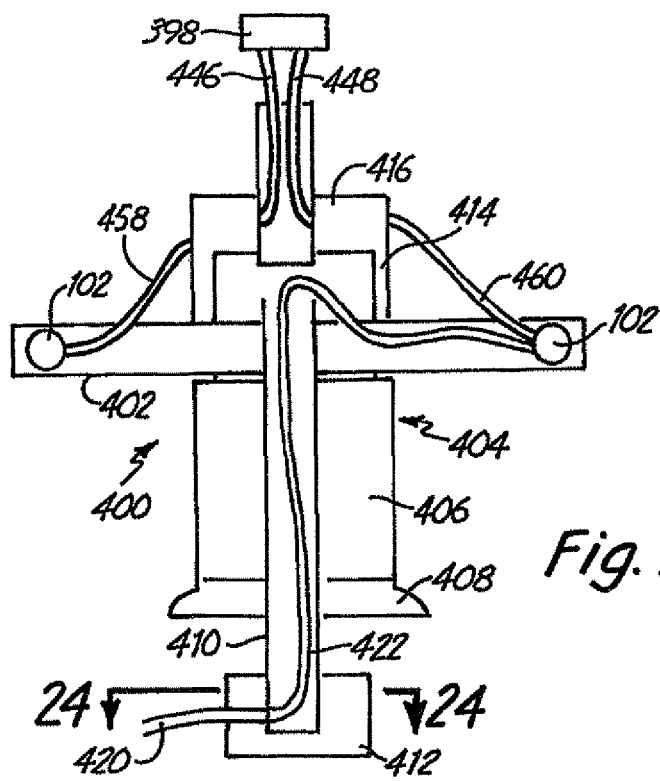
FIG. 23 is a sectional view of a flow system with an electric slip ring and a fluid slip ring, in which the section is taken through the center of the apparatus.

However, if the rotating tube 102 rotates in one direction more than 360 degree, flexible tubing, 392, 394 can become tangled. The connection between tubing 392, 394 and fluid exchange apparatus can be constructed with a slip ring to prevent tangling of tubing. Slip ring assemblies allow for the connection of medical devices to stationary electrical wires as well as for fluid exchange. A cross section of a flow system with slip rings is depicted in FIG. 23. Flow system 400 includes a rotating turntable 402 supporting tubing 102. Motor 404 controls the rotation of turntable 402. Motor 404 includes rotating support 406 and a stationary base 408. Shaft 410 extends through motor 404 and turntable 402, and shaft 410 rotates with turntable 402. Shaft 410 connects with electrical slip ring 412. Platform 414 connects to and rotates with turntable 402. Fluid slip ring 416 rests on platform 414.

Figure 24:
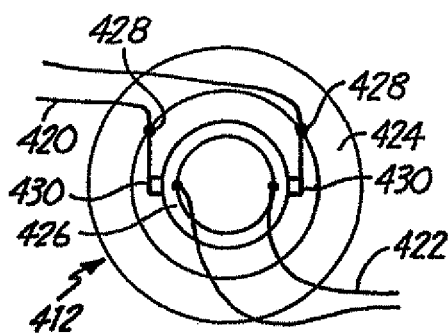
FIG. 24 is a sectional view of the electric slip ring of FIG. 23 taken along line 24-24.

Stationary wires 420 and rotating wires 422 connect with electrical slip ring 412. Stationary wires connect with a stationary electrical device and/or power source and do not rotate with turntable 402. Rotating wires 422 lead up shaft 410 and connect with electrical components rotating in the flow system and possibly a medical device within tube 102. Referring to FIG. 24, slip ring 412 includes a stationary ring 424 and a rotating ring 426 that connects with shaft 410. Stationary wires 420 connect with electrical terminals 428 on stationary ring 424. Rotating ring 426 or a portion thereof is electrically conductive and connected to rotating wires 422. Electrically conductive brushes 430 connect terminals 428 with rotating ring 426 and provide electrical continuity between stationary wires 420 and rotating wires 422. A bearing assembly provides for relative rotation between rotating ring 426 and stationary ring 424. Electrical slip ring assemblies are available commercially from Fibricast, Inc., South El Monte, Calif.

Figure 25:
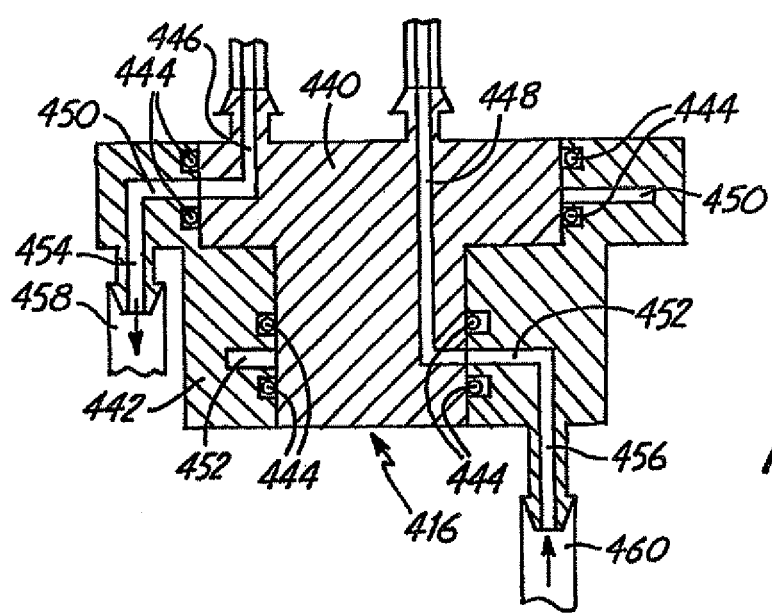
FIG. 25 is a sectional view of the fluid slip ring of FIG. 23.

An embodiment of fluid slip ring 416 is shown in FIG. 25. Fluid slip ring 416 includes a stationary inner core 440 and rotating ring 442 which rotates around inner core 440. O-rings 444 or the like provide a fluid tight seal between rotating ring 442 and inner core 440. In this embodiment, inner core 440 includes two stationary fluid conduits 446, 448. As shown in FIG. 23, through a connection with fluid exchange apparatus 398, stationary fluid conduit 446 provides for the addition of fluid to tube 102, and stationary fluid conduit 448 provides for removal of fluid from tube 102. Rotating ring 442 includes annular cavities 450, 452 in communication with stationary fluid conduits 446, 448, respectively. Annular cavities 450, 452, respectively, connect with rotating fluid conduits 454, 456. Rotating fluid conduits 454, 456 connect with tubing 458, 460 connecting with tube 102. Thus, fluid from a rotational or translational flow system can be exchanged from a stationary fluid exchange system.

Fluid exchange apparatus 398 can include various components to exchange fluids such as a fluid supply reservoir and a waste container. In some embodiments, a dialysis set-up can be used with fluid from tube 102 passing through a dialysis cartridge contacting an appropriate fluid to exchange nutrients and remove waste. The fluid contacting the dialysis cartridge can be replaced when appropriate to maintain the desired composition. Other structures for fluid exchange apparatus can be used, such as embodiments that fully exchange fluids. For example, one or more pumps, such as peristaltic pumps, can be used to pump a new fluid into the system while system pressure and or other pumps remove the existing fluid. The fluid that is exchanged can include, for example, cell suspensions, body fluids, such as plasma or whole blood, culture media, saline, water, or any desired priming, processing or rinsing agent.

The use of fluid slip rings to deliver a fluid from a stationary source into a rotating flow system can also be useful for the delivery of gas to an oxygenator residing in the rotating flow system. Likewise, it can also be useful for delivery temperature controlling liquid to a heat exchanger residing in the rotating flow system.

Based on the selected materials, appropriate chemical, heat or radiation based sterilization approaches can be used to sterilize the system components. Assembly of sterile components under aseptic conditions will provide a sterile system for medical device testing and/or production. Alternatively, the components can be assembled and then sterilized using appropriate sterilization approaches.

The adjustments of parameters, such as temperature, pressure, flow rate, gas content, gas composition, and the like, can be adjusted manually by an operator based on observations, sensor readings, and the like to achieve desired operating conditions. Specifically, suitable temperature sensors, pressure sensors, pH sensors, gas sensors and the like can be placed within the flow system to monitor and maintain control over system parameters. In alternative embodiments, a microprocessor based controller can be used to monitor and/or adjust one or more operating parameters. The control functions can be integrated through the use of commercially available laboratory designed software using Unix®, Windows®, or other computer operating systems. This is true for the embodiments above and the embodiments described below.

Embodiments With Pulsed Flow With a Continuous Pump

In alternative embodiments, a continuous flow pump is used to circulate fluid through a closed loop having branched paths. The circulating fluid can be pulsed past or through a medical device mount by controlling flow with valves leading into alternative branches. Each branched path can contain a check valve, such as a valved prosthesis. If the medical device is a valved prosthesis mounted as a check valve in a path, pressure relief tubing can be connected with the medical device mount to create a pressure differential across the medical device when flow from the pump into the branch is stopped.

Figure 26:
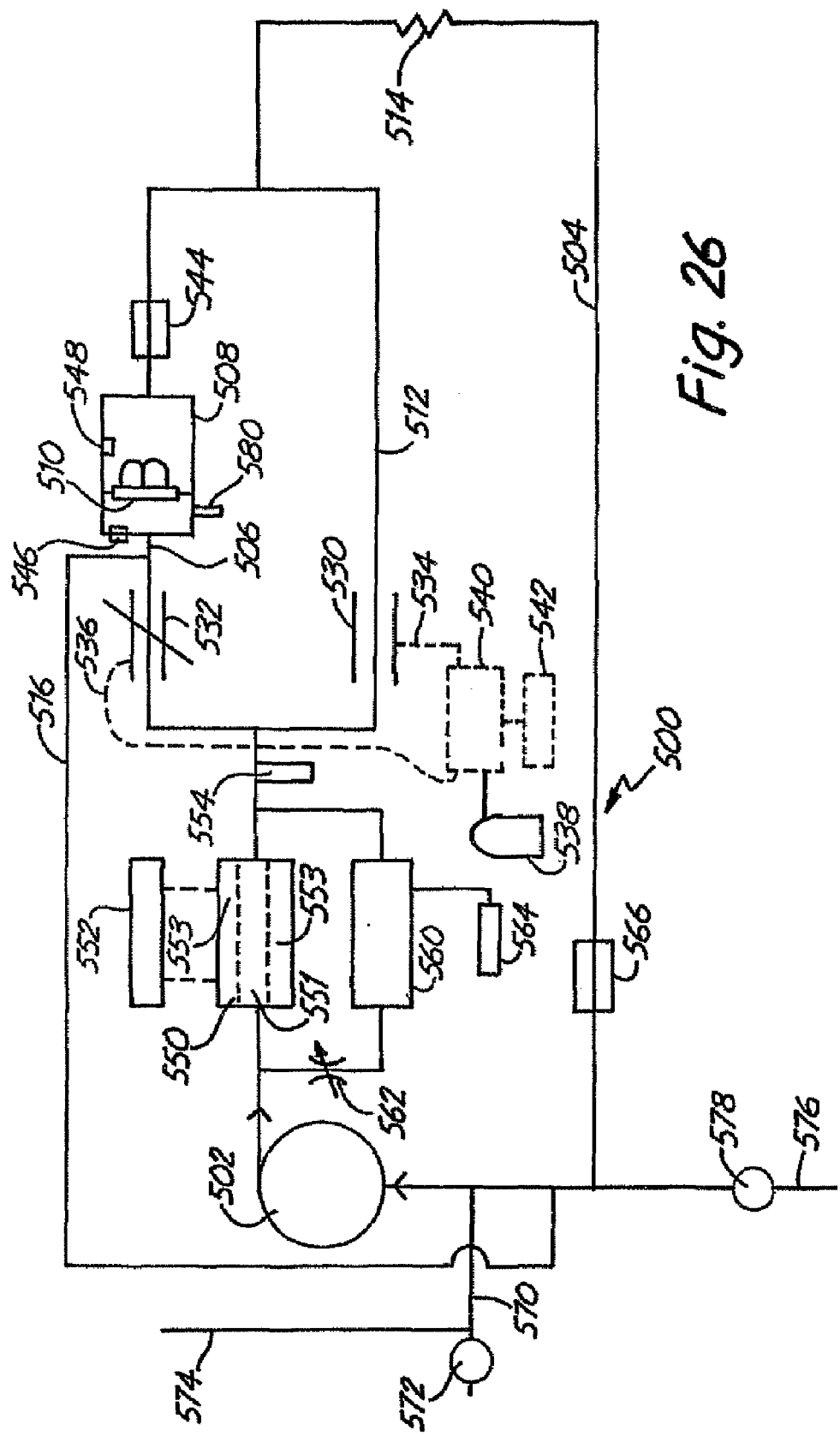
FIG. 26 is a diagram of a flow system having a continuous flow pump.

An embodiment of a flow system using a continuous pump is shown in FIG. 26. Flow system 500 includes a pump 502 connected to a flow loop 504. Preferred pumps, such as centrifugal pumps, continuously deliver fluid. Fluid from pump 502 can flow through channel 506 with a mount 508 supporting medical device 510, such as a valved prosthesis. Medical device mount 508 generally holds medical device 510 within the flow of channel 506. In preferred embodiments, medical device 510 is a valved prosthesis positioned such that the flow through channel 506 passes through the valve. This preferred embodiment is the focus of the discussion below with medical device 510 being referred to as valved prosthesis 510.

Similarly, fluid from pump 502 can flow into by-pass tubing 512. A flow restrictor 514 controls the fluid flow from channel 506 and by-pass tubing 512 back to pump 502 along flow loop 504. Flow restrictor 514 results in a pressure drop on the downstream side of flow restrictor 514 relative to the upstream side. One end of pressure relief tubing 516 connects to channel 506 between flow control valve 532 and mount 508, and the other end connects to the downstream side of flow restrictor 514. For the circulation of viable cells, it is preferred that the flow path has an inner diameter of at least about 0.5 inch (1.3 cm) to reduce cell damage due to elevated velocities.

Flow control valves 530, 532 control flow into channel 506 and by-pass tubing 512, respectively. In preferred embodiments, flow control valves 530, 532 are controlled automatically to open and close at periodic intervals. In one embodiment, flow control valves 530, 532 are pinch clamps. Flow control valves (pinch clamps) 530, 532 can be connected to air cylinders 534, 536, respectively. Air cylinders 534, 536 can be venting cylinders that provide a high degree of control over the force and speed by which pinch clamps restrict fluid flow to either channel 506 or by-pass tubing 512. Suitable air cylinders are available from Bimba Manufacturing Co., Monee, Ill. Diverting gas from a gas supply 538 to open and close air cylinders 534, 536 can be accomplished with gas valves 540. Timer 542, such as an electronic timer, actuates gas valves 540 to provide the desired opening and closing rate of the pinch clamps 530, 532. In preferred embodiments, the pinch clamp upstream of mount 508 opens and closes from 50 to 120 times per minute to simulate the in vivo pulse rates of a beating heart. The average flow rate through valved prosthesis 510 is controlled by varying the speed of pump 502 and the pulse frequency. In preferred embodiments, the average flow rate through valved prosthesis 510 is in a range between about 1.0 liter per minute (l/min) to about 5.0 l/min. Flow rate can be measured with a flow rate sensor 544, such as an ultrasonic probe from Transonic Systems, Ithaca, N.Y. For embodiments having blood circulated within flow loop 504, the total volume of fluid within flow loop 504 preferably is less than about 500 ml, such that whole blood from a single donor can be used.

In operation, fluid delivered from pump 502 flows alternatively into channel 506 or by-pass tubing 512. When pinch clamp 532 is open and pinch clamp 530 is closed, fluid flows through channel 506 and through valved prosthesis 510. The flow opens valved prosthesis 510. After flowing through valved prosthesis 510, the flow continues through flow restrictor 514 and returns to pump 502. Pressure relief tubing 516 has a very small inner diameter, preferably less than about 25% of the diameter of channel 506, such that flow through pressure relief tubing is more restricted than flow through flow restrictor 514. When valve 530 opens and valve 532 closes, fluid delivered from pump 502 passes through by-pass tubing 512.

The magnitude of the pressure differential across valved prosthesis 510 can be controlled by adjusting flow restrictor 514. More resistance to the flow by restrictor 514 causes a larger pressure differential across valved prosthesis 510. The downstream side of valved prosthesis 510 is at the higher inlet pressure of flow restrictor 514 while the upstream side of valved prosthesis 510 is at the lower outlet pressure of flow restrictor 514. In preferred embodiments, the pressure differential across the closed valved prosthesis can be varied from about 20 mm of Hg (Torr) to about 120 mm of Hg (Torr), and preferably from about 70 mm of Hg (Torr) to about 100 mm of Hg (Torr). The pressure differential can be measured with pressure sensors 546, 548 placed on respective sides of the valved prostheses. Commercial pressure sensors can be used.

Additional components can be included to maintain the properties of the fluid within the flow system. For example, flow system 500 can include a heat exchanger 550. Fluid within flow loop 504 flows through the tube side 551 of heat exchanger 550. Fluid, the temperature of which is controlled by heating/cooling element 552, flows through the shell side 553 of heat exchanger 550. In some embodiments, heating/cooling element 552 is a temperature controlled water bath. Temperature sensor 554 is connected to flow loop 504 to monitor the temperature of the circulating fluid. Based on the reading of temperature sensor 554, heating/cooling element 552 provides hot or cold fluid to heat exchanger 550 to correspondingly heat or cool the fluid circulating in flow loop 504. Thus, the temperature of the fluid can be maintained within a desired range, as described above.

In addition, flow loop 504 can be connected to an oxygenator 560 to adjust the gas content in the flowing fluid. A flow regulator 562 may be used to control flow from flow loop 502 into oxygenator 560. Oxygenator 560, for example, can include a gas permeable membrane or tubing to provide for gas exchange. Commercial oxygenators are available. Flow regulator 562 can be, for example, a clamp on the tubing or a peristaltic pump. A peristaltic pump can be advantageous if pressure spikes occur when either pinch clamp 530 or 532 is released. In that event, negative pressure is prevented from occurring within oxygenator 560, thus preventing gas from entering the fluid passing through oxygenator 560. Oxygenator 560 can be combined with heat exchanger 550, such that flow through the combined device provides both gas exchange and temperature control.

Oxygenator 560 can be used to control the oxygen tension in fluid within flow loop 504. Varying the concentration of gases within oxygenator 560 directly varies the oxygen tension of the fluid. Generally, gas flow into oxygenator 560 is supplied by gas supply 564. Gas supply 564 preferably is a combination of oxygen, nitrogen and carbon dioxide that is blended, humidified, filtered for particulates and sterile filtered prior to entering oxygenator 560.

The monitoring of pH, and partial pressures of carbon dioxide and oxygen in the flowing fluid can be measured with commercially available sensors, such as CDI 400 Systems from Terumo Corp., Japan. Sensor 566 can be inserted into flow loop 504, as shown in FIG. 26. A signal from sensor 566 can be used to regulate the gas composition entering oxygenator 560.

Fluid can be delivered into flow loop 504 through inlet line 570. The delivery of fluid into flow loop 504 can use gravity or a pump 572, such as a peristaltic pump. Gases can be vented through vent line 574. Vent line 574 preferably is connected to a sterile filter to prevent contamination of flow loop 504. Vent line 574 can be filled with fluid to control the base line pressure within the system. Vent line 574 can also be used to store excess fluid to replace or offset fluid removed from flow loop 504. Fluid can be removed from flow loop 504 from sample port 580 or through outlet line 576. Removal of fluid can be based on gravity, aspiration or a pump 578, such as a peristaltic pump.

Figure 27:
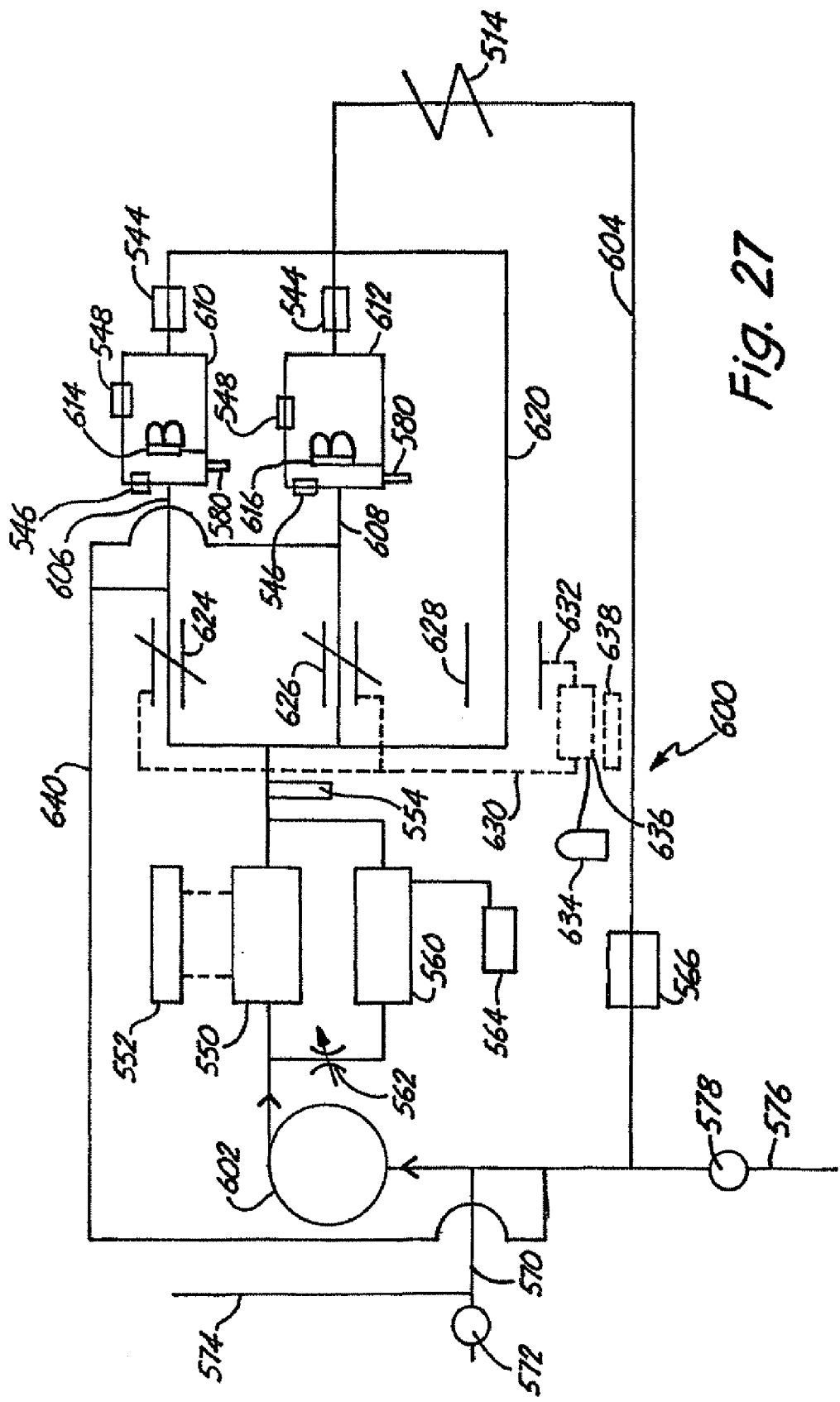
FIG. 27 is a diagram of a flow system having a continuous pump and two mounts for valved prostheses.

An alternative embodiment of a flow system with a continuous pump and a plurality of medical device mounts is shown in FIG. 27. Flow system 600 includes a continuous flow pump 602 and a flow loop 604. Flow system 600 is comprised of many of the features in flow system 500 in FIG. 26. However, flow system 600 includes two channels 606, 608 with medical device mounts 610, 612, in contrast with flow system 500 which only includes a single channel, channel 506, with a medical device mount 508. Pressure relief tubing 640 connects with both channels 606, 608.

Medical device mounts 610, 612 generally hold a medical devices 614, 616 within the flow of channels 606, 608, respectively. Preferably, medical devices 614, 616 are valved prostheses positioned to have the flow through channels 606, 608 passing through the respective valves. The discussion below focuses on these preferred embodiments, with medical devices 614, 616 being referred to as valved prostheses 614, 616.

By-pass tubing 620 connects to flow loop 604 in parallel with channels 606, 608 as an alternative path. Flow control valves 624, 626, 628 control the flow into channels 606, 608 and by-pass tubing 620, respectively. In some embodiments, flow control valves 624, 626, 628 are pinch clamps, although other valves can be used. As described above with respect to FIG. 26, the opening and closing of pinch clamps can be controlled with air cylinders. In some embodiments, flow control valves 624, 626 are connected to a single air cylinder 630 such that flow control valves 624, 626 open and close together. Alternatively, each flow control valve 624, 626 can be separately connected to an air cylinder 630, 632. Flow control valve 628 is connected to a second air cylinder 632. Diverting gas from a gas supply 634 to open and close air cylinders 630, 632 can be accomplished with gas valves 636. Timer 638 actuates gas valves 636 to provide the desired pulse rate of the fluid flow by opening and closing flow control valves 624, 626, 628.

In operation, flow control valves 624, 626 and 628 can be controlled to produce a desired flow pattern. Generally, one or more of the valves are closed while one or more of the valves are open. In some embodiments, both flow control valves 624, 626 are open when valve 628 is closed or vice versa. The magnitude of the pressure differential is again controlled by the resistance to flow provided by flow restrictor 514. In alternative embodiments, flow control valves 624, 626, 628 are individually opened while the other two valves are closed. For example, each flow control valve can be open approximately ⅓ of the time, at which time the other two flow control valves are closed. Care should be taken to configure pressure relief tubing 640 such that each line emanating from flow through channels 606, 608 has an equal inner diameter and length. Such a configuration ensures an equal response time for opening and closing valved prostheses 614, 616.

Medical Devices

Relevant biocompatible articles include all medical devices that contact body fluids and/or tissue as well as structures for performing cell cultures, such as cell culture support matrices. Implanted medical devices and components thereof include, without limitation, prostheses such as artificial organs including artificial hearts, ventricular assist devices, anatomical reconstruction prostheses such as artificial heart valves, heart valve stents, valve leaflets, orifice rings of mechanical heart valves, pericardial patches, surgical patches, coronary stents, vascular grafts, vascular, cardiovascular and structural stents, vascular and cardiovascular shunts, biological conduits, pledgets, suture, annuloplasty rings, stents, staples, connectors, valved grafts, dermal grafts for wound healing, orthopedic and spinal implants, intrauterine devices (IUDs), urinary stents, permanently indwelling pericardial devices, clips, bone prostheses, skin prostheses, ligament prostheses, tendon prostheses, liver assist devices, pancreas/islet cell implants, and combinations thereof.

Percutaneous medical devices include, without limitation, angioplasty balloons, catheters of various types, cannulas, drainage tubes such as chest tubes, and catheter cuffs. Catheters can be used for accessing various bodily systems, such as the vascular system, the gastrointestinal tract, the urinary system and the reproductive systems.

The medical device can be a cell culture support matrix. In tissue culture applications, the flow systems can be used to culture cells under a wide range of conditions, including representative physiological conditions. Applications of cell cultures operating under near physiological conditions include the repair of defects or abnormal tissue in the body. In tissue culture applications requiring unstructured or monolayer architecture, a substrate, such as tissue culture treated polystyrene, can be used for the cell culture support matrix.

In many desirable applications, a three dimensional culture support matrix is required to form three dimensional structures analogous to cell or tissue counterparts in vivo, such as nerve tissue, blood vessels, cartilage, tendons, ligaments, bone, heart valves, other hard and soft tissues, and for applications relating to the study of such tissue. In applications in which three dimensional culture is desired, the cell culture support matrix is initially formed to have the overall desired shape. Thus, in the formation of a prosthesis, the three dimensional matrix for cell colonization should have the approximate dimensions desired for the ultimate prosthesis.

Suitable three dimensional cell culture support matrices can be comprised of collagen gel, cellulose sponge, collagen coated cellulose sponge, gelatin sponge, collagen crosslinked to form one side into a nonporous skin, porous polyvinyl formal resin, synthetic and biological matrices including resorbable matrices, as described below or any other suitable matrix material. Collagen gel is particularly suitable for soft and hard tissue augmentation. Cellulose sponge is useful for nerve repair and vascular repair. Methods for forming these matrices include methods known in the art, for example, as described in Biomedical Engineering Handbook, Joseph D. Bronzino, editor-in-chief, CRC Press (1995), incorporated herein by reference.

Other suitable matrix materials include, for example, materials formed from intestinal submucosa. Examples of such material is described in U.S. Pat. No. 5,997,575 to Whitson et al., entitled "Perforated Submucosal Tissue Graft Constructs," incorporated herein by reference, and U.S. Pat. No. 5,993,844 to Abraham et al., entitled "Chemical Treatment, Without Detergents Or Enzymes, Of Tissue To Form An Acellular, Collagenous Matrix," incorporated herein by reference.

Preferred medical devices are valved grafts, such as valved vein grafts and heart valve prostheses. The valved graft protheses can be cell culture matrices shaped like a valve and/or simulating a valve, which become seeded with cells during the cell culture process. The heart valve prosthesis can be designed as a replacement for any heart valve, i.e., an aortic valve, a mitral valve, a tricuspid valve, or a pulmonary valve. Some heart valve prostheses have rigid occluders that pivot to open and close the valve while other heart valve prostheses have flexible leaflets of polymer or tissue that open and close in response to pressure differentials. With any valved prosthesis, the valve acts as a one-way check valve that opens for fluid flow in one direction and closes to limit fluid flow in the opposite direction.

In some preferred embodiments, the medical device includes cells or tissue at least as a component. Tissue-based medical devices can be evaluated or prepared through the use of the flow systems described herein, as described below. Tissue-based heart valve prostheses are of particular interest.

For tissue containing embodiments, appropriate bioprosthetic tissue materials can be formed from natural materials, synthetic tissue matrices, tissue equivalents and combinations thereof. Natural, i.e., biological, material for use in the invention includes relatively intact (cellular) tissue as well as modified (decellularized) tissue. These tissues may be obtained from, for example, natural heart valves, portions of natural heart valves such as roots, walls and leaflets, pericardial tissues such as pericardial patches, connective tissues, bypass grafts, tendons, ligaments, skin patches, blood vessels, cartilage, dura mater, liver, pancreas, lung, kidney, skin, bone, fascia, submucosa, umbilical tissues, and the like. Some tissue materials are particularly useful for the formation of tissue heart valve prostheses. Tissues include genetically engineered tissues.

Natural tissues are derived from a particular animal species, typically mammalian, such as human, bovine, porcine, canine, seal or kangaroo. These tissues may include a whole organ or a functional component thereof, including allografts and autografts. Suitable natural tissues generally include collagen-containing material. Natural tissue is typically, but not necessarily, soft tissue. The tissue can be decellularized. Decellularization approaches are described, for example, U.S. Pat. No. 5,855,620 to Bishopric et al., entitled "Matrix Substrate for a Viable Body Tissue-Derived Prosthesis and Method for Making the Same," incorporated herein by reference.

Appropriate tissues also include tissue equivalents such as tissue-engineered material involving a cell-repopulated matrix, which can be formed from a polymer or from a natural tissue. Also, synthetic tissue matrices can be formed from extracellular matrix proteins that are crosslinked to form a tissue matrix. Extracellular matrix proteins are commercially available. Synthetic tissue matrices may approximate decellularized natural tissue.

Tissues can be used in either crosslinked or uncrosslinked form, depending on the type of tissue, the use and other factors. Tissues can be fixed by crosslinking. Fixation provides mechanical stabilization, for example, by preventing enzymatic degradation of the tissue. Glutaraldehyde is typically used for fixation, but other difunctional aldehydes or epoxides can be used.

The tissue material can form the entire medical device or it can form portions of the medical device. Similarly, different portions of crosslinked tissue material can be combined to form the medical device.

It may be desirable to use prostheses with no tissue component to examine how the prosthesis responds to contact with blood or other fluids, which could include viable cells. For example, a ceramic/carbon based mechanical heart valve has been developed in which the material is modified with biological modifiers to induce association of viable cells with the material. Suitable carbon materials and carbon coatings include, for example, pyrolytic carbon, glassy carbon, graphite, amorphous carbon, carbon nitride and diamond-like carbon. Preferred biological response modifiers include, for example, extracellular matrix proteins and vascular endothelial growth factors. Thus, a mechanical heart valve is formed that can host endothelial cells modifying the surface properties of the material or a portion thereof. It may be desirable to test these mechanical valves or to seed the valved prostheses with viable cells using the flow system of the invention. These modified mechanical heart valve prostheses are described further in copending and commonly assigned U.S. patent application Ser. No. 09/459,451 to Carlyle et al., entitled "MEDICAL ARTICLES PREPARED FOR CELL ADHESION," incorporated herein by reference.

Other suitable biocompatible materials for use in the medical devices include, for example, polymers, metals, ceramics, carbon materials and combinations thereof. Suitable metals include biocompatible metals, such as, stainless steel, titanium, cobalt alloys, such as Elgiloy®, a cobalt-chromium-nickel alloy, and MP35N, a nickel-cobalt-chromium-molybdenum alloy, and Nitinol®, a nickel-titanium alloy. Suitable ceramic materials include, for example, silicon carbides or metal carbides, hydroxyapatite and alumina. Suitable carbon materials include, for example, pyrolytic carbon, diamond-like carbon and graphite.

Polymeric materials can be classified as resorbable polymers as well as non-resorbable polymers, with some related polymers falling in each class. Similarly, suitable polymers may be synthetic, biological polymers or modified biological polymers. The polymeric materials can be woven into a mesh to form a matrix or substrate. Alternatively, the polymer materials can be molded or cast into appropriate forms, such as films and non-woven meshes, and blown into foams. Appropriate non-resorbable, synthetic polymers include, without limitation, polyamides (e.g., nylon), polyesters, polystyrenes, polyacrylates, vinyl polymers {e.g., polyethylene, polytetrafluoroethylene (Teflon®), polypropylene, poly vinyl alcohol, chlorosulphonated polyolefins, poly (vinyl imidizol), polyvinyl fluoride and polyvinyl chloride}, polycarbonates, polyethylene oxide, polyurethanes, poly dimethyl siloxanes, cellulose acetates, polymethyl methacrylates, ethylene vinyl acetates, polysulfones, nitrocelluloses and similar copolymers.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, prolamines, keratin, gelatin, polyamino acids, polysaccharides (e.g., alginate, heparin, cellulose and starch) and copolymers thereof.

Other suitable polymers include natural or synthetic resorbable polymers such as polysaccharides (dextran, hydroxyethyl starch, oxidized cellulose, chitosan, alginates), gelatin, collagen, albumin, derivatives of gelatin, fibrin/fibrinogen, transductional elastic protein-based polymers, polyvinylpyrrolidone, polycarbonates, polyamides, polyarylates, synthetic poly(amino acids), poly(p-dioxane), genetically engineered protein polymers, polyoxamers, polyacetals, polyurethanes, polyhydroxyalkanoate, poly(propylene fumarate), poly(alkylcyanoacrylates) polycyanoacrylates, polyacrylates, polyvinylalcohol, poly[N-(2-hydroxylpropyl) methacrylamide], polyglycols, polyesters, poly (orthoesters), poly(ester amides), polyanhydrides. Resorbable polyesters include, for example, poly (hydroxy acids) and copolymers thereof, poly($\epsilon$-caprolactone), poly (dimethyl glycolic acid), and poly (hydroxy butyrate). Preferred resorbable polymers include, for example, D, L-polylactic acid (PLA), L-polylactic acid (PLA), poly(glycolic acid) (PGA), and copolymers of L-lactic acid, D-lactic acid and/or glycolic acid (PLA/PGA copolymers).

Biological Response Modifiers

The medical device can be associated with a biological response modifier that is either released into the flowing fluid or bound to the medical device to affect the interaction of the fluid with the medical device. In particular, the tissue can be treated to stimulate the association of desirable cells with the tissue, to promote the proliferation of associated cells and/or to reduce calcification of the tissue following implantation.

For example, a substrate can be associated with one or more growth factors, such as vascular endothelial growth factor (VEGF) and/or fibroblast growth factor, and/or attraction compounds that recruit cells, including precursor cells, to the tissue. VEGF refers to a family of polypeptides that have been found to preferentially stimulate growth of vascular endothelial cells over other cells, such as smooth muscle cells. Several iso-forms of VEGF have been identified. VEGF has also been referred to as vascular permeability factor. Human recombinant VEGF$_{165}$ is available commercially from R&D Systems, Minneapolis, Minn.

The use of VEGF in the production of tissue containing prostheses has been described further in copending and commonly assigned U.S. patent application Ser. No. 09/014,087 to Carlyle et al., entitled "Prostheses With Associated Growth Factors," and Ser. No. 09/186,810 to Carlyle et al., entitled "Prostheses With Associated Growth Factors," both of which are incorporated herein by reference.

For the attraction of precursor cells, desirable precursor cells include both stem cells and progenitor cells that have the potential to differentiate into the cells of interest, including fibroblasts or endothelial cells. Some precursor cells circulate in a patient's blood stream, while others may be mobilized from other sites in the body or infused into the circulation. These precursor cells are thus available to colonize suitable blood contacting substrates. Suitable precursor cells can be selected from the blood stream and associated with a substrate that serves as the foundation for a viable prosthetic tissue. To initiate the colonization by the precursor cells, an attraction compound can be associated with the substrate material. Circulating precursor cells may be removed from circulation by the attraction compound and become associated with the substrate. The use of attraction compounds, such as antibodies and ligands, to associate precursor cells with a substrate is described further in copending and commonly assigned U.S. patent application Ser. No. 09/203,052 to Carlyle et al., entitled "Substrates For Forming Synthetic Tissue," incorporated herein by reference.

The association of a treatment compound or compounds, e.g., a growth factor and/or an attraction compound, with a substrate each may involve direct attachment, application of a coating including an adhesive or binder, or chemical binding involving a binding agent in addition to the attraction compound/response modifier.

Direct attachment entails combining the substrate with a solution of the treatment compound(s) without the use of an additional chemical binder. With the use of an adhesive, the treatment compound(s) associates with the substrate due to incorporation into the structure of the cured adhesive. Preferred adhesives include, for example, biologic glues such as fibrin glue, and the like. Fibrin glue can be formed from the polymerization of fibrinogen and thrombin. Suitable fibrin glues are available from, for example, Immuno AG, Austria and Zymogenetics, Seattle, Wash.

In other embodiments, the association of a treatment compound(s) with the substrate involves chemical binding initiated by a selected chemical reagent, a chemical binding agent. In contrast to the use of an adhesive, chemical binding involves specific molecular interactions with compositions in the crosslinked tissue, rather than a collective adhesion. Chemical binding can involve covalent bonding, a plurality of noncovalent chemical interactions, or a combination of both covalent and noncovalent interactions. Noncovalent chemical interactions include hydrogen bonding, van der Waals interactions and molecular rearrangements, which characterize specific binding interactions, such as antibody-antigen interactions, protein-receptor binding and enzyme-substrate associations.

Also, it may be desirable to contact the tissue with one or more calcification reducing agents. Suitable calcification reducing agents include detergents (e.g., sodium dodecyl sulfate), toluidine blue, diphosphonates, and multivalent cations, especially $Al^{+3}$, $Mg^{+2}$ or $Fe^{+3}$, or corresponding metals that can oxidize to form the multivalent metal cations. The effectiveness of $AlCl_3$ and $FeCl_3$ in reducing calcification of crosslinked tissue is described in U.S. Pat. No. 5,368,608 to Levy et al., entitled "Calcification-Resistant Materials and Methods of Making Same Through Use of Multivalent Cations," incorporated herein by reference. The association of anticalcific elemental metals is described in copending and commonly assigned U.S. patent application Ser. No. 09/017,185 to Ogle et al., entitled "CALCIFICATION-RESISTANT MEDICAL ARTICLES," incorporated herein by reference.

Use of Flow System

The flow systems/bioreactors described herein can be used to test medical devices and/or to produce medical devices for distribution and use. Testing can involve evaluation of, for example, the fluid dynamic or rheological properties, the effects of the medical device on viable cells, colonization of a medical device by bacteria/fungi, cell association with the medical device and/or performance of the medical device with the passage of time, which can deteriorate due to calcification and/or wear of the device. Testing of performance parameters can involve measurements of forces at a medical device during pulsed flow. Production of a medical device with the flow system can involve cell seeding as well as surface modification and/or sterilization prior to subsequent patient use.

The fluid used within the flow system generally is selected to be consistent with the intended use of the system. In some embodiments, the fluid contains viable cells. Whether or not the fluid includes viable cells, the fluid can be selected to support the continued viability of viable cells. Whole blood has the advantage that it contains cells, cellular elements and plasma proteins at physiological concentrations.

For cell seeding from blood, it may be desirable to obtain the blood from a single individual such that the cells and other blood constituents are self-compatible. For embodiments involving cell seeding as part of prosthesis production, preferably the blood originates from the ultimate recipient such that the seeded prosthesis does not induce an immune response following implantation.

For surface modification of the material, the fluid can be appropriately selected. For example, the fluid can be a solution containing a crosslinking agent, a growth factor, and antiseptic agents, such as aqueous alcohol. Alcohols are also useful to reduce cytotoxicity of aldehyde crosslinked tissues. Particularly preferred solutions for reducing or eliminating aldehyde cytotoxicity are described further in copending and commonly assigned U.S. patent application Ser. No. 09/480,437 to Ashworth et al., entitled "Biocompatible Prosthetic Tissue," incorporated herein by reference.

If the fluid within the flow system contains cells, the cells can be selected for the ultimate purpose of the medical device. Suitable cells include, for example, endothelial cells, fibroblast cells, stem cells, progenitor cells, hepatocytes, adipocytes, osteocytes, osteoclasts, neurons, mesenchymal cells, dendritic cells, chondrocytes, epithelial cells, muscle cells, and islet (pancreas) cells. Various cell types and cell culture media are available commercially from vendors, such as Clonetics, San Diego, Calif. With the proper selection of cells, organs or surrogate organs can be generated for implantation and/or external use to supplement or replace damaged or diseased natural organs.

Especially for valved prostheses, it may be desirable to use the flow system to examine the fluid dynamic properties, i.e., the flow rates, pressure differential across the valve, and the opening and/or closing rates, of the valved prosthesis. Using whole blood as the circulating fluid, fluid flow can be examined under conditions that more closely resemble physiological conditions. Other fluids can be used as an alternative or in addition to blood to examine how fluid properties affect flow and/or to assist with visualization of the flow. In particular, use of a medical device mount that is at least partially transparent allows for visual observation of a valved prosthesis during pulsed flow.

It may be desirable to examine how the medical device responds to contact with body fluids, such as blood, plasma, or other fluids. When fluids containing viable cells are circulated in the flow system, the effects of the medical device on viable cells can be examined. For example, cells can be examined for damage resulting from operation of the valve under different conditions, such as flow rates, pressure differential, and opening and/or closing rates. Thus, valve designs can specifically incorporate features that are less likely to cause cell damage following implantation into a patient.

Furthermore, the flow system can be used to evaluate the performance of a medical device following the passage of time. In particular, the flow properties of valved prostheses can be tested after accelerated fatigue testing to simulate valve performance following years of use. Since the devices are functioning under representative physiological conditions, potential deterioration can be more reflective of in vivo performance. In general, the medical device may or may not be first subjected to an accelerated fatigue tester prior to further evaluation of temporal changes under physiological conditions.

Another use of the flow system/bioreactor involving medical device contact with cell-containing fluids is cell seeding. The flow system can be used to simulate in vivo colonization of a medical device within a patient following implantation. Specifically, since the flow system mimics physiological conditions, cell seeding can be evaluated under near physiological conditions, especially with the circulation of whole blood. In particular, the pulsed flow in the flow system provides stresses similar to the in vivo environment.

The flow system can also be used to produce a prosthesis with viable cells in vitro for subsequent implantation within a patient. For prosthesis production by cell seeding, in order to reduce the possibility of immune system rejection, viable cells used for in vitro cell seeding preferably are autologous cells, i.e., cells from the recipient patient. Cell seeding could be performed with mature cells, immature cells or a combination thereof.

Medical devices or components thereof can be incubated with cells for a period of hours to days to allow for cell seeding. Cell seeding provides attachment of cells resulting in colonization of the surface of the prosthetic material either before or after implantation into the patient. By performing attachment of viable cells under physiological conditions, the cells colonizing the material may function more similarly to native tissue.

The flow system can be used to examine the thrombogenicity of a valved prosthesis. When using blood or blood components as the circulating fluid, thrombogenicity can be examined by detecting platelet deposition and/or clot formation using microscopic inspection. In particular, valve designs, tissue fixation, valve coatings and valve materials generally can be evaluated for their impact on thrombogenicity.

In addition, calcification of a medical device, such as a valved prosthesis, can be evaluated. For these evaluations, the fluid can be saline or medium rich in calcium or phosphates. The amount of calcium deposition can be evaluated, for example, using inductively coupled plasma-atomic emission spectroscopy, for example with an ICP-AES Atom-Scan 16™ (Thermo Jarrell Ash Corp., Franklin, Mass.). Also, scanning electron microscopy can be used to evaluate calcification.

The flow system can be used for a wide variety of cell culture applications in which it is desirable to culture cells under physiologically representative conditions.

The apparatuses and methods described herein can be used to circulate fluids containing cells under conditions that result in low cell damage. In particular, the apparatuses are suitable for the circulation of blood, especially, human blood. System sterility can be maintained for extended periods of time. The systems can operate over a wide range of parameters relating to the operating conditions with various values of pH, flow rates, temperature, pressure, fluid composition, gas composition and the like.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. An apparatus comprising:
a valve holder block that comprises:
a first port and a second port for receiving a fluid;
a first flow passageway extending between the first and the second ports;
a bypass channel extending between the ports and in fluid communication with the first flow passageway, the bypass channel having at least one factor that affects flow relative to the corresponding factors of the first flow passageway; and
a first check valve positioned in the first flow passageway which restricts flow in a first direction; and
a conduit forming a loop comprising a first conduit end coupled to the first port and a second conduit end coupled to the second port; and
an assembly that moves the conduit and the valve holder block to induce relative bidirectional motion of the fluid according to the factors.

2. The apparatus of claim 1 wherein the factor is selected from the group of the diameter of the bypass channel, the angle between the bypass channel and the first flow passageway, and the surface finish of the bypass channel.

3. The apparatus of claim 1, wherein the first check valve is positioned in a first valve mount, and the assembly moves the conduit to induce relative motion of the fluid relative to the valve mount.

4. The apparatus of claim 3 further comprising a medical device attached to the valve mount.

5. The apparatus of claim 4 wherein the medical device is releasably mounted on the valve mount.

6. The apparatus of claim 4 wherein the medical device is a valved prosthesis.

7. The apparatus of claim 6 wherein the valved prosthesis comprises leaflets.

8. The apparatus of claim 4 wherein the medical device comprises tissue.

9. The apparatus of claim 4 wherein the medical device comprises a cell culture support matrix.

10. The apparatus of claim 9 wherein the cell culture support matrix comprises a three dimensional support matrix.

11. The apparatus of claim 1 wherein the fluid comprises blood.

12. The apparatus of claim 1 wherein the fluid comprises viable cells.

13. The apparatus of claim 1 wherein the fluid comprises a tissue crosslinking agent.

14. The apparatus of claim 1 wherein the fluid comprises cell culture medium.

15. The apparatus of claim 1 wherein the assembly comprises a pneumatic actuator.

16. The apparatus of claim 1 wherein the assembly comprises a servo motor.

17. The apparatus of claim 1 wherein the bypass channel is in fluid communication with the conduit on each side of the valve mount.

18. The apparatus of claim 17 wherein the bypass channel comprises a second check valve, the second check valve restricting flow in an opposite direction of the flow through the first check valve.

19. The apparatus of claim 1 wherein the motion induced by the assembly is rotational motion.

20. The apparatus of claim 1, further comprising a plurality of valve mounts.

21. The apparatus of claim 1, wherein the assembly moves the conduit along with the valve mount to induce relative pulsatile motion of The fluid relative to the valve mount.

22. The apparatus of claim 1, wherein the first check valve is positioned in a first valve mount, and the assembly moves the conduit along with the valve mount to induce relative motion of the fluid relative to the valve mount, and the assembly drives pulsatile fluid flow by moving the conduit with periodic reversals of direction.

23. The apparatus of claim 22 wherein the motion induced by the assembly is rotational motion.

24. The apparatus of claim 22 wherein the motion induced by the assembly is translational motion.

25. The apparatus of claim 22 further comprising a medical device attached to the valve mount.

26. The apparatus of claim 25 wherein the medical device is releasably mounted on the valve mount.

27. The apparatus of claim 25 wherein the medical device comprises a cell culture support matrix.

28. The apparatus of claim 27 wherein the cell culture support matrix comprises a three dimensional support matrix.

29. The apparatus of claim 22 wherein the fluid comprises blood.

30. The apparatus of claim 22 wherein the fluid comprises cell culture medium.

31. The apparatus of claim 22 wherein the assembly comprises a pneumatic actuator.

32. The apparatus of claim 22 wherein the bypass channel is in fluid communication with the conduit on each side of the valve mount.

33. The apparatus of claim 1 wherein the conduit is supported on a movable platform.

34. The apparatus of claim 1, wherein the first check valve is positioned in a first valve mount, and a the assembly moves the conduit along with the valve mount to induce relative motion of the fluid relative to the valve mount, and the motion induced by the assembly is translational motion.

35. The apparatus of claim 34 wherein the assembly drives pulsatile fluid flow by moving the conduit with periodic reversals of motion.

36. The apparatus of claim 34 further comprising a medical device attached to the valve mount.

37. The apparatus of claim 36 wherein the medical device is releasably mounted on the valve mount.

38. The apparatus of claim 36 wherein the medical device comprises a cell culture support matrix.

39. The apparatus of claim 38 wherein the cell vulture support matrix comprises a three-dimensional support matrix.

40. The apparatus of claim 34 wherein the assembly comprises a pneumatic actuator.

41. The apparatus of claim 34 wherein the fluid comprises blood.

42. The apparatus of claim 34 wherein the fluid comprises cell culture medium.

43. The apparatus of claim 1 wherein the conduit is in fluid communication with a fluid slip ring.

44. The apparatus of claim 1, wherein the fluid comprises cells and the conduit is mounted on the assembly that moves the conduit to induce flow of the fluid along an axis of the fluid relative to the conduit wherein the cells comprise endothelial cells, fibroblast cells, stem cells, progenitor cells, hepatocytes, adipocytes, osteocytes, osteoclasts, neurons, mesenchymal cells, dendritic cells, chondrocytes, epithelial cells, muscle cells, or islet (pancreas) cells.

* * * * *

UNITED STATES PATENT AND TRADEMARK OFFICE
CERTIFICATE OF CORRECTION

PATENT NO. : 7,326,564 B2  Page 1 of 1
APPLICATION NO. : 09/789130
DATED : February 5, 2008
INVENTOR(S) : Beverley I. Lundell et al.

It is certified that error appears in the above-identified patent and that said Letters Patent is hereby corrected as shown below:

Col. 25, line 67, change "The" to --the--.

Col. 26, line 47, change "vulture" to --culture--.

Signed and Sealed this

Fifteenth Day of July, 2008

JON W. DUDAS
*Director of the United States Patent and Trademark Office*